United States Patent [19]
McCoy et al.

[11] Patent Number: 5,270,181
[45] Date of Patent: Dec. 14, 1993

[54] PEPTIDE AND PROTEIN FUSIONS TO THIOREDOXIN AND THIOREDOXIN-LIKE MOLECULES

[75] Inventors: John McCoy, Reading; Edward R. LaVallie, Tewksbury, both of Mass.

[73] Assignee: Genetics Institute, Inc., Cambridge, Mass.

[21] Appl. No.: 745,382

[22] Filed: Aug. 14, 1991

Related U.S. Application Data

[63] Continuation-in-part of Ser. No. 652,531, Feb. 6, 1991, abandoned.

[51] Int. Cl.$^5$ .................. C12P 21/02; C12N 15/11; C12N 15/24; C12N 15/62
[52] U.S. Cl. .................. 435/69.7; 435/320.1; 435/243; 435/252.3; 435/252.33; 435/254.11; 536/23.4; 935/10; 935/27; 935/6.6; 935/6.9; 935/72; 935/73
[58] Field of Search .......... 536/27; 435/69.1, 69.7, 435/243, 240.1, 320.1, 252.3, 252.33, 255; 935/10, 27, 72

[56] References Cited

U.S. PATENT DOCUMENTS

| | | | |
|---|---|---|---|
| 4,745,069 | 5/1988 | Mayne et al. | 435/320.1 |
| 4,769,326 | 9/1988 | Rutter | 435/68.1 |
| 4,801,536 | 1/1989 | Stahl et al. | 435/69.1 |
| 4,828,988 | 5/1989 | Bollen et al. | 435/68.1 |
| 5,011,772 | 4/1991 | Recsei | 435/69.52 |

FOREIGN PATENT DOCUMENTS

| | | |
|---|---|---|
| 267703 | 5/1988 | European Pat. Off. |
| 2180539A | 4/1987 | United Kingdom |
| PCT/US87/-03113 | 6/1988 | World Int. Prop. O. |

OTHER PUBLICATIONS

Kamo et al. (1989) Eur. J. Biochem. 182: 315–322.
Donald B. Smith et al., *Gene* 67:31–40 (1988).
Catherine H. Schein, *Bio/Technology* 7:1141–1147 (1989).
Arne Holmgren, *J. Biol. Chem.* 264(24):13963–13966 (1989).
Jeffrey C. Edman et al., *Nature* 317:267–270 (1985).
C. Frank Bennett et al., *Nature* 334:268–279 (1988).
Richard A. Mazzarella et al., *J. Biol. Chem.* 265(2):1094–1101 (1990).
Naomi Wakasugi et al., *Proc. Natl. Acad. Sci. USA* 87:8282–8286 (1990).
H. Eklund et al., *EMBO J.* 3(7):1443–1449 (1984).
P. Riggs, *Current Protocols in Molecular Biology* 2(10):16.4.1–16.8.1 (1990).
M. E. Bayer, *J. Gen. Microbiol.* 53:395–404 (1968).
M. E. Bayer, *J. Bacteriology* 93(3):1104–1112 (1967).
C. A. Lunn et al., "Thioredoxin and Glutaredoxin Systems: Structure and Function", pp. 165–176.
C. A. Lunn et al., *J. Biol. Chem.* 257(19): 11424–11430 (1982).
G. R. Jacobson et al., *Biochemistry* 15(11):2297–2303 (1976).
P. Denefle et al., *Gene* 85:499–510 (1989).
E. Joseph-Liauzun et al., *Gene* 86:291–295 (1990).
T. A. Rosenwasser et al., *J. Biol. Chem.* 265(22):13066–13073 (1990).

*Primary Examiner*—Robert A. Wax
*Assistant Examiner*—Gabriele E. Bugaisky
*Attorney, Agent, or Firm*—Luann Cserr; Maureen C. Meinert; Bruce M. Eisen

[57] ABSTRACT

This invention provides a fusion molecule comprising a DNA sequence encoding a thioredoxin-like protein fused to the DNA sequence encoding a selected heterologous peptide or protein. The peptide or protein may be fused to the amino terminus of the thioredoxin-like molecule, the carboxyl terminus of the thioredoxin-like molecule, or within the thioredoxin-like molecule, for example at the active-site loop of said molecule. Expression of this fusion molecule under the control of a regulatory sequence capable of directing its expression in a desired host cell, produces high levels of stable and soluble fusion protein. The fusion protein, located in the bacterial cytoplasm, may be selectively released from the cell by osmotic shock or freeze/thaw procedures. It may be optionally cleaved to liberate the soluble, correctly folded heterologous protein from the thioredoxin-like portion.

30 Claims, 12 Drawing Sheets

FIG. 1 pALtrxA/EK/IL11ΔPro-581

SEQ ID NO:13 and SEQ ID NO:14

| | | | | |
|---|---|---|---|---|
| GACGAAAGGG | CCTCGTGATA | CGCCTATTTT | TATAGGTTAA | 40 |
| TGTCATGATA | ATAATGGTTT | CTTAGACGTC | AGGTGGCACT | 80 |
| TTTCGGGGAA | ATGTGCGCGG | AACCCCTATT | TGTTTATTTT | 120 |
| TCTAAATACA | TTCAAATATG | TATCCGCTCA | TGAGACAATA | 160 |
| ACCCTGATAA | ATGCTTCAAT | AATATTGAAA | AAGGAAGAGT | 200 |
| ATGAGTATTC | AACATTTCCG | TGTCGCCCTT | ATTCCCTTTT | 240 |
| TTGCGGCATT | TTGCCTTCCT | GTTTTGCTC | ACCCAGAAAC | 280 |
| GCTGGTGAAA | GTAAAAGATG | CTGAAGATCA | GTTGGGTGCA | 320 |
| CGAGTGGGTT | ACATCGAACT | GGATCTCAAC | AGCGGTAAGA | 360 |
| TCCTTGAGAG | TTTTCGCCCC | GAAGAACGTT | TTCCAATGAT | 400 |
| GAGCACTTTT | AAAGTTCTGC | TATGTGGCGC | GGTATTATCC | 440 |
| CGTATTGACG | CCGGGCAAGA | GCAACTCGGT | CGCCGCATAC | 480 |
| ACTATTCTCA | GAATGACTTG | GTTGAGTACT | CACCAGTCAC | 520 |
| AGAAAAGCAT | CTTACGGATG | GCATGACAGT | AAGAGAATTA | 560 |
| TGCAGTGCTG | CCATAACCAT | GAGTGATAAC | ACTGCGGCCA | 600 |
| ACTTACTTCT | GACAACGATC | GGAGGACCGA | AGGAGCTAAC | 640 |
| CGCTTTTTTG | CACAACATGG | GGGATCATGT | AACTCGCCTT | 680 |
| GATCGTTGGG | AACCGGAGCT | GAATGAAGCC | ATACCAAACG | 720 |
| ACGAGCGTGA | CACCACGATG | CCTGTAGCAA | TGGCAACAAC | 760 |
| GTTGCGCAAA | CTATTAACTG | GCGAACTACT | TACTCTAGCT | 800 |
| TCCCGGCAAC | AATTAATAGA | CTGGATGGAG | GCGGATAAAG | 840 |
| TTGCAGGACC | ACTTCTGCGC | TCGGCCCTTC | CGGCTGGCTG | 880 |
| GTTTATTGCT | GATAAATCTG | GAGCCGGTGA | GCGTGGGTCT | 920 |
| CGCGGTATCA | TTGCAGCACT | GGGGCCAGAT | GGTAAGCCCT | 960 |
| CCCGTATCGT | AGTTATCTAC | ACGACGGGGA | GTCAGGCAAC | 1000 |

FIG. 1A

| | | | | |
|---|---|---|---|---|
| TATGGATGAA | CGAAATAGAC | AGATCGCTGA | GATAGGTGCC | 1040 |
| TCACTGATTA | AGCATTGGTA | ACTGTCAGAC | CAAGTTTACT | 1080 |
| CATATATACT | TTAGATTGAT | TTAAAACTTC | ATTTTTAATT | 1120 |
| TAAAAGGATC | TAGGTGAAGA | TCCTTTTTGA | TAATCTCATG | 1160 |
| ACCAAAATCC | CTTAACGTGA | GTTTTCGTTC | CACTGAGCGT | 1200 |
| CAGACCCCGT | AGAAAAGATC | AAAGGATCTT | CTTGAGATCC | 1240 |
| TTTTTTTCTG | CGCGTAATCT | GCTGCTTGCA | AACAAAAAAA | 1280 |
| CCACCGCTAC | CAGCGGTGGT | TTGTTTGCCG | GATCAAGAGC | 1320 |
| TACCAACTCT | TTTTCCGAAG | GTAACTGGCT | TCAGCAGAGC | 1360 |
| GCAGATACCA | AATACTGTCC | TTCTAGTGTA | GCCGTAGTTA | 1400 |
| GGCCACCACT | TCAAGAACTC | TGTAGCACCG | CCTACATACC | 1440 |
| TCGCTCTGCT | AATCCTGTTA | CCAGTGGCTG | CTGCCAGTGG | 1480 |
| CGATAAGTCG | TGTCTTACCG | GGTTGGACTC | AAGACGATAG | 1520 |
| TTACCGGATA | AGGCGCAGCG | GTCGGGCTGA | ACGGGGGGTT | 1560 |
| CGTGCACACA | GCCCAGCTTG | GAGCGAACGA | CCTACACCGA | 1600 |
| ACTGAGATAC | CTACAGCGTG | AGCATTGAGA | AAGCGCCACG | 1640 |
| CTTCCCGAAG | GGAGAAAGGC | GGACAGGTAT | CCGGTAAGCG | 1680 |
| GCAGGGTCGG | AACAGGAGAG | CGCACGAGGG | AGCTTCCAGG | 1720 |
| GGGAAACGCC | TGGTATCTTT | ATAGTCCTGT | CGGGTTTCGC | 1760 |
| CACCTCTGAC | TTGAGCGTCG | ATTTTTGTGA | TGCTCGTCAG | 1800 |
| GGGGGCGGAG | CCTATGGAAA | AACGCCAGCA | ACGCGGCCTT | 1840 |
| TTTACGGTTC | CTGGCCTTTT | GCTGGCCTTT | TGCTCACATG | 1880 |
| TTCTTTCCTG | CGTTATCCCC | TGATTCTGTG | GATAACCGTA | 1920 |
| TTACCGCCTT | TGAGTGAGCT | GATACCGCTC | GCCGCAGCCG | 1960 |
| AACGACCGAG | CGCAGCGAGT | CAGTGAGCGA | GGAAGCGGAA | 2000 |
| GAGCGCCCAA | TACGCAAACC | GCCTCTCCCC | GCGCGTTGGC | 2040 |
| CGATTCATTA | ATGCAGAATT | GATCTCTCAC | CTACCAAACA | 2080 |

FIG. 1B

```
ATGCCCCCCT GCAAAAAATA AATTCATATA AAAAACATAC                                      2120

AGATAACCAT CTGCGGTGAT AAATTATCTC TGGCGGTGTT                                      2160

GACATAAATA CCACTGGCGG TGATACTGAG CACATCAGCA                                      2200

GGACGCACTG ACCACCATGA ATTCAAGAAG GAGATATACA                                      2240

T ATG AGC GAT AAA ATT ATT CAC CTG ACT GAC GAC                                    2274
  Met Ser Asp Lys Ile Ile His Leu Thr Asp Asp
  1               5                   10

AGT TTT GAC ACG GAT GTA CTC AAA GCG GAC GGG                                      2307
Ser Phe Asp Thr Asp Val Leu Lys Ala Asp Gly
            15              20

GCG ATC CTC GTC GAT TTC TGG GCA GAG TGG TGC                                      2340
Ala Ile Leu Val Asp Phe Trp Ala Glu Trp Cys
        25              30

GGT CCG TGC AAA ATG ATC GCC CCG ATT CTG GAT                                      2373
Gly Pro Cys Lys Met Ile Ala Pro Ile Leu Asp
    35              40

GAA ATC GCT GAC GAA TAT CAG GGC AAA CTG ACC                                      2406
Glu Ile Ala Asp Glu Tyr Gln Gly Lys Leu Thr
45              50                       55

GTT GCA AAA CTG AAC ATC GAT CAA AAC CCT GGC                                      2439
Val Ala Lys Leu Asn Ile Asp Gln Asn Pro Gly
                    60              65

ACT GCG CCG AAA TAT GGC ATC CGT GGT ATC CCG                                      2472
Thr Ala Pro Lys Tyr Gly Ile Arg Gly Ile Pro
            70              75

ACT CTG CTG CTG TTC AAA AAC GGT GAA GTG GCG                                      2505
Thr Leu Leu Leu Phe Lys Asn Gly Glu Val Ala
        80              85

GCA ACC AAA GTG GGT GCA CTG TCT AAA GGT CAG                                      2538
Ala Thr Lys Val Gly Ala Leu Ser Lys Gly Gln
        90              95

TTG AAA GAG TTC CTC GAC GCT AAC CTG GCC GGT                                      2571
Leu Lys Glu Phe Leu Asp Ala Asn Leu Ala Gly
100             105                 110

TCT GGT TCT GGT GAT GAC GAT GAC AAA GGT CCA                                      2604
Ser Gly Ser Gly Asp Asp Asp Asp Lys Gly Pro
                115                 120
```

FIG. 1C

| | | | | | | | | | | |
|---|---|---|---|---|---|---|---|---|---|---|
| CCA | CCA | GGT | CCA | CCT | CGA | GTT | TCC | CCA | GAC CCT | 2637 |
| Pro | Pro | Gly<br>125 | Pro | Pro | Arg | Val | Ser | Pro<br>130 | Asp Pro | |
| CGG | GCC | GAG | CTG | GAC | AGC | ACC | GTG | CTC | CTG ACC | 2670 |
| Arg | Ala | Glu<br>135 | Leu | Asp | Ser | Thr | Val | Leu<br>140 | Leu Thr | |
| CGC | TCT | CTC | CTG | GCG | GAC | ACG | CGG | CAG | CTG GCT | 2703 |
| Arg | Ser<br>145 | Leu | Leu | Ala | Asp | Thr<br>150 | Arg | Gln | Leu Ala | |
| GCA | CAG | CTG | AGG | GAC | AAA | TTC | CCA | GCT | GAC GGG | 2736 |
| Ala<br>155 | Gln | Leu | Arg | Asp | Lys<br>160 | Phe | Pro | Ala | Asp Gly<br>165 | |
| GAC | CAC | AAC | CTG | GAT | TCC | CTG | CCC | ACC | CTG GCC | 2769 |
| Asp | His | Asn | Leu | Asp<br>170 | Ser | Leu | Pro | Thr | Leu Ala<br>175 | |
| ATG | AGT | GCG | GGG | GCA | CTG | GGA | GCT | CTA | CAG CTC | 2802 |
| Met | Ser | Ala | Gly<br>180 | Ala | Leu | Gly | Ala | Leu | Gln Leu<br>185 | |
| CCA | GGT | GTG | CTG | ACA | AGG | CTG | CGA | GCG | GAC CTA | 2835 |
| Pro | Gly | Val<br>190 | Leu | Thr | Arg | Leu | Arg | Ala<br>195 | Asp Leu | |
| CTG | TCC | TAC | CTG | CGG | CAC | GTG | CAG | TGG | CTG CGC | 2868 |
| Leu | Ser<br>200 | Tyr | Leu | Arg | His | Val<br>205 | Gln | Trp | Leu Arg | |
| CGG | GCA | GGT | GGC | TCT | TCC | CTG | AAG | ACC | CTG GAG | 2901 |
| Arg<br>210 | Ala | Gly | Gly | Ser | Ser<br>215 | Leu | Lys | Thr | Leu Glu<br>220 | |
| CCC | GAG | CTG | GGC | ACC | CTG | CAG | GCC | CGA | CTG GAC | 2934 |
| Pro | Glu | Leu | Gly | Thr<br>225 | Leu | Gln | Ala | Arg | Leu Asp<br>230 | |
| CGG | CTG | CTG | CGC | CGG | CTG | CAG | CTC | CTG | ATG TCC | 2967 |
| Arg | Leu | Leu | Arg | Arg<br>235 | Leu | Gln | Leu | Leu | Met Ser<br>240 | |
| CGC | CTG | GCC | CTG | CCC | CAG | CCA | CCC | CCG | GAC CCG | 3000 |
| Arg | Leu | Ala | Leu<br>245 | Pro | Gln | Pro | Pro | Asp<br>250 | Pro | |
| CCG | GCG | CCC | CCG | CTG | GCG | CCC | CCC | TCC | TCA GCC | 3033 |
| Pro | Ala | Pro<br>255 | Pro | Leu | Ala | Pro | Pro | Ser<br>260 | Ser Ala | |

FIG. 1D

| | |
|---|---|
| TGG GGG GGC ATC AGG GCC GCC CAC GCC ATC CTG<br>Trp Gly Gly Ile Arg Ala Ala His Ala Ile Leu<br>265                           270                          275 | 3066 |
| GGG GGG CTG CAC CTG ACA CTT GAC TGG GCC GTG<br>Gly Gly Leu His Leu Thr Leu Asp Trp Ala Val<br>                          280                           285 | 3099 |
| AGG GGA CTG CTG CTG CTG AAG ACT CGG CTG TGA<br>Arg Gly Leu Leu Leu Leu Lys Thr Arg Leu<br>                      290                        295 | 3132 |
| AAGCTTATCG ATACCGTCGA CCTGCAGTAA TCGTACAGGG | 3172 |
| TAGTACAAAT AAAAAAGGCA CGTCAGATGA CGTGCCTTTT | 3212 |
| TTCTTGTGAG CAGTAAGCTT GGCACTGGCC GTCGTTTTAC | 3252 |
| AACGTCGTGA CTGGGAAAAC CCTGGCGTTA CCCAACTTAA | 3292 |
| TCGCCTTGCA GCACATCCCC CTTTCGCCAG CTGGCGTAAT | 3332 |
| AGCGAAGAGG CCCGCACCGA TCGCCCTTCC CAACAGTTGC | 3372 |
| GCAGCCTGAA TGGCGAATGG CGCCTGATGC GGTATTTTCT | 3412 |
| CCTTACGCAT CTGTGCGGTA TTTCACACCG CATATATGGT | 3452 |
| GCACTCTCAG TACAATCTGC TCTGATGCCG CATAGTTAAG | 3492 |
| CCAGCCCCGA CACCCGCCAA CACCCGCTGA CGCGCCCTGA | 3532 |
| CGGGCTTGTC TGCTCCCGGC ATCCGCTTAC AGACAAGCTG | 3572 |
| TGACCGTCTC CGGGAGCTGC ATGTGTCAGA GGTTTTCACC | 3612 |
| GTCATCACCG AAACGCGCGA | 3632 |

FIG. 2

MIP-1α

SEQ ID NO:15 and SEQ ID NO:16

| GCA | CCA | CTT | GCT | GCT | GAC | ACG | CCG | ACC | GCC | TGC | TGC | 36 |
|---|---|---|---|---|---|---|---|---|---|---|---|---|
| Ala | Pro | Leu | Ala | Ala | Asp | Thr | Pro | Thr | Ala | Cys | Cys | |
| 1 | | | | 5 | | | | | 10 | | | |

| TTC | AGC | TAC | ACC | TCC | CGA | CAG | ATT | CCA | CAG | AAT | TTC | 72 |
|---|---|---|---|---|---|---|---|---|---|---|---|---|
| Phe | Ser | Tyr | Thr | Ser | Arg | Gln | Ile | Pro | Gln | Asn | Phe | |
| | | 15 | | | | | 20 | | | | | |

| ATA | GCT | GAC | TAC | TTT | GAG | ACG | AGC | AGC | CAG | TGC | TCC | 109 |
|---|---|---|---|---|---|---|---|---|---|---|---|---|
| Ile | Ala | Asp | Tyr | Phe | Glu | Thr | Ser | Ser | Gln | Cys | Ser | |
| 25 | | | | | 30 | | | | | 35 | | |

| AAG | CCC | AGT | GTC | ATC | TTC | CTA | ACC | AAG | AGA | GGC | CGG | 145 |
|---|---|---|---|---|---|---|---|---|---|---|---|---|
| Lys | Pro | Ser | Val | Ile | Phe | Leu | Thr | Lys | Arg | Gly | Arg | |
| | | | 40 | | | | | 45 | | | | |

| CAG | GTC | TGT | GCT | GAC | CCC | AGT | GAG | GAG | TGG | GTC | CAG | 181 |
|---|---|---|---|---|---|---|---|---|---|---|---|---|
| Gln | Val | Cys | Ala | Asp | Pro | Ser | Glu | Glu | Trp | Val | Gln | |
| | 50 | | | | | 55 | | | | | 60 | |

| AAA | TAC | GTC | AGT | GAC | CTG | GAG | CTG | AGT | GCC | TAA | | 214 |
|---|---|---|---|---|---|---|---|---|---|---|---|---|
| Lys | Thr | Val | Ser | Asp | Leu | Glu | Leu | Ser | Ala | | | |
| | | | | 65 | | | | | 70 | | | |

FIG. 3

BMP-2

SEQ ID NO:17 and SEQ ID NO:18

| CAA | GCT | AAA | CAT | AAA | CAA | CGT | AAA | CGT | CTG | AAA | TCT | 36 |
| Gln | Ala | Lys | His | Lys | Gln | Arg | Lys | Arg | Leu | Lys | Ser | |
| 1 | | | | 5 | | | | | 10 | | | |

| AGC | TGT | AAG | AGA | CAC | CCT | TTG | TAC | GTG | GAC | TTC | AGT | 72 |
| Ser | Cys | Lys | Arg | His | Pro | Leu | Tyr | Val | Asp | Phe | Ser | |
| | | 15 | | | | | 20 | | | | | |

| GAC | GTG | GGG | TGG | AAT | GAC | TGG | ATT | GTG | GCT | CCC | CCG | 109 |
| Asp | Val | Gly | Trp | Asn | Asp | Trp | Ile | Val | Ala | Pro | Pro | |
| 25 | | | | | 30 | | | | | 35 | | |

| GGG | TAT | CAC | GCC | TTT | TAC | TGC | CAC | GGA | GAA | TGC | CCT | 145 |
| Gly | Tyr | His | Ala | Phe | Tyr | Cys | His | Gly | Glu | Cys | Pro | |
| | | | 40 | | | | | 45 | | | | |

| TTT | CCT | CTG | GCT | GAT | CAT | CTG | AAC | TCC | ACT | AAT | CAT | 181 |
| Phe | Pro | Leu | Ala | Asp | His | Leu | Asn | Ser | Thr | Asn | His | |
| | 50 | | | | | 55 | | | | | 60 | |

| GCC | ATT | GTT | CAG | ACG | TTG | GTC | AAC | TCT | GTT | AAC | TCT | 217 |
| Ala | Ile | Val | Gln | Thr | Leu | Val | Asn | Ser | Val | Asn | Ser | |
| | | | | 65 | | | | | 70 | | | |

| AAG | ATT | CCT | AAG | GCA | TGC | TGT | GTC | CCG | ACA | GAA | CTC | 253 |
| Lys | Ile | Pro | Lys | Ala | Cys | Cys | Val | Pro | Thr | Glu | Leu | |
| | | 75 | | | | | 80 | | | | | |

| AGT | GCT | ATC | TCG | ATG | CTG | TAC | CTT | GAC | GAG | AAT | GAA | 289 |
| Ser | Ala | Ile | Ser | Met | Leu | Tyr | Leu | Asp | Glu | Asn | Glu | |
| 85 | | | | | 90 | | | | | 95 | | |

| AAG | GTT | GTA | TTA | AAG | AAC | TAT | CAG | GAC | ATG | GTT | GTG | 325 |
| Lys | Val | Val | Leu | Lys | Asn | Tyr | Gln | Asp | Met | Val | Val | |
| | | | 100 | | | | | 105 | | | | |

| GAG | GGT | TGT | GGG | TGT | CGC | TAG | | | | | | 346 |
| Glu | Gly | Cys | Gly | Cys | Arg | | | | | | | |
| | 110 | | | | | | | | | | | |

FIG. 4

INSERTION OF AN ENTEROKINASE SITE INTO
THE ACTIVE-SITE LOOP OF E.COLI THIOREDOXIN (trxA)

```
                                    RsrII
                                      |
                       ....GAGTGGTGCGGTCCGTGCAAAATG....
trxA active            ------------------------------
site loop              ....CTCACCACGCCAGGCACGTTTTAC....

....E    W    C    G    P    C    K    M ....
                           31                                 38

....GAGTGGTGCG            GTCCGTGCAAAATG....
RsrII cut     --------------             ---------------
              ....CTCACCACGCCAG          GCACGTTTTAC....

....E    W    C    G           P    C    K    M ....
                  31                                          38
```

Enterokinase site
(13 residues)

```
        gtcactccGACTACAAAGACGACGACGACAAAgcttctg
                ---------------------------------
        tgaggCTGATGTTTCTGCTGCTGCTGTTTcgaagaccag ....H    S    D    Y    K    D    D    D    K    A    S    G...
                                              ^
                                           ^
                                        ^
                                  cleavage site
```

FIG. 5

RANDOM PEPTIDE INSERTIONS INTO THE ACTIVE-SITE
LOOP OF E.COLI THIOREDOXIN (trxA)

```
                              RsrII
                                |
                   ....GAGTGGTGCGGTCCGTGCAAAATG....
    trxA active    ---------------------------
    site loop      ....CTCACCACGCCAGGCACGTTTTAC....

....E  W  C  G  P  C  K  M  ....
                       31                    38
```

```
                ....GAGTGGTGCG          GTCCGTGCAAAATG....
    RsrII cut   ----------              --------------
                ....CTCACCACGCCAG           GCACGTTTTAC....

....E  W  C  G          P  C  K  M  ....
                    31                              38
```

```
                        (AvaII)            AvaII
              5'           |                 |
    3'
    oligos        GACTGACTGGTCCG...(N36)...GGTCCTCAGTCAGTCAG
                  ------------------------------------------
    CCAGGAGTCAGTCAGTC
    3'                    5'
```

```
    random             GTCCG...(N36)...G
    duplex             -----------------
                       GC...(N36)...CCAG
``` insertion into trxA active site loop

```
    ....GAGTGGTGCGGTCCG...(N36)...GGTCCGTGCAAAATG....
        --------------------------------------------
    ....CTCACCACGCCAGGC...(N36)...CCAGGCACGTTTAC....

SEQ ID NO:19 and SEQ ID NO:20

```
                      5                        10
ATG GCT CCA GTA CCT CCA GGT GAA GAT TCT AAA GAT GTA    39
Met Ala Pro Val Pro Pro Gly Glu Asp Ser Lys Asp Val 15                   20                   25
GCC GCC CCA CAC AGA CAG CCA CTC ACC TCT TCA GAA CGA    78
Ala Ala Pro His Arg Gln Pro Leu Thr Ser Ser Glu Arg 30                   35
ATT GAC AAA CAA ATT CGG TAC ATC CTC GAC GGC ATC TCA   117
Ile Asp Lys Gln Ile Arg Tyr Ile Leu Asp Gly Ile Ser 40                   45                   50
GCC CTG AGA AAG GAG ACA TGT AAC AAG AGT AAC ATG TGT   156
Ala Leu Arg Lys Glu Thr Cys Asn Lys Ser Asn Met Cys 55                   60
GAA AGC AGC AAA GAG GCA CTG GCA GAA AAC AAC CTG AAC   195
Glu Ser Ser Lys Glu Ala Leu Ala Glu Asn Asn Leu Asn 65                   70                   75
CTT CCA AAG ATG GCT GAA AAA GAT GGA TGC TTC CAA TCT   234
Leu Pro Lys Met Ala Glu Lys Asp Gly Cys Phe Gln Ser 80                   85                   90
GGA TTC AAT GAG GAG ACT TGC CTG GTG AAA ATC ATC ACT   273
Gly Phe Asn Glu Glu Thr Cys Leu Val Lys Ile Ile Thr 95                  100
GGT CTT TTG GAG TTT GAG GTA TAC CTA GAG TAC CTC CAG   312
Gly Leu Leu Glu Phe Glu Val Tyr Leu Glu Thr Leu Gln 105                  110                  115
AAC AGA TTT GAG AGT AGT GAG GAA CAA GCC AGA GCT GTG   351
Asn Arg Phe Glu Ser Ser Glu Glu Gln Ala Arg Ala Val
```

FIG. 6A

```
            120                      125
CAG ATG AGT ACA AAA GTC CTG ATC CAG TTC CTG CAG AAA    390
Gln Met Ser Thr Lys Val Leu Ile Gln Phe Leu Gln Lys 130                  140                  150
AAG GCA AAG AAT CTA GAT GCA ATA ACC ACC CCT GAC CCA    429
Lys Ala Lys Asn Leu Asp Ala Ile Thr Thr Pro Asp Pro 155                  160
ACC ACA AAT GCC AGC CTG CTG ACG AAG CTG CAG GCA CAG    468
Thr Thr Asn Ala Ser Leu Leu Thr Lys Leu Gln Ala Gln 170                  175                  180
AAC CAG TGG CTG CAG GAC ATG ACA ACT CAT CTC ATT CTG    507
Asn Gln Trp Leu Gln Asp Met Thr Thr His Leu Ile Leu 185                  190
CGC AGC TTT AAG GAG TTC CTG CAG TCC AGC CTG AGG GCT    546
Arg Ser Phe Lys Glu Phe Leu Gln Ser Ser Leu Arg Ala

195
CTT CGG CAA ATG TAG                                    561
Leu Arg Gln Met  *
```

FIG. 7

(SEQ ID NO: 23)
(SEQ ID NO: 24)

```
  1 GAAGAAGTTT CTGAATATTG TAGCCACATG ATTGGGAGTG GACACCTGCA
 51 GTCTCTGCAG CGGCTGATTG ACAGTCAGAT GGAGACCTCG TGCCAAATTA
101 CATTTGAGTT TGTAGACCAG GAACAGTTGA AAGATCCAGT GTGCTACCTT
151 AAGAAGGCAT TTCTCCTGGT ACAAGACATA ATGGAGGACA CCATGCGCTT
201 CAGAGATAAC ACCCCCAATG CCATCGCCAT TGTGCAGCTG CAGGAACTCT
251 CTTTGAGGCT GAAGAGCTGC TTCACCAAGG ATTATGAAGA GCATGACAAG
301 GCCTGCGTCC GAACTTTCTA TGAGACACCT CTCCAGTTGC TGGAGAAGGT
351 CAAGAATGTC TTTAATGAAA CAAAGAATCT CCTTGACAAG GACTGGAATA
401 TTTTCAGCAA GAACTGCAAC AACAGCTTTG CTGAATGCTC CAGCCAAGAT
451 GTGGTGACCA AGCCTGATTG CAACTGCCTG TACCCCAAAG CCATCCCTAG
501 CAGTGACCCG GCCTCTGTCT CCCCTCATCA GCCCCTCGCC CCTCCATGG
551 CCCCTGTGGC TGGCTTGACC TGGGAGGACT CTGAGGGAAC TGAGGGCAGC
601 TCCCTCTTGC CTGGTGAGCA GCCCCTGCAC ACAGTGGATC CAGGCAGTGC
651 CAAGCAGCGG CCACCCAGG
```

PEPTIDE AND PROTEIN FUSIONS TO THIOREDOXIN AND THIOREDOXIN-LIKE MOLECULES

This is a continuation-in-part of U.S. application Ser. No. 07/652,531, filed Feb. 6, 1991 (abandoned).

The present invention relates generally to the production of fusion proteins in prokaryotic and eukaryotic cells. More specifically, the invention relates to the expression in host cells of recombinant fusion sequences comprising thioredoxin or thioredoxin-like sequences fused to sequences for selected heterologous peptides or proteins, and the use of such fusion molecules to increase the production, activity, stability or solubility of recombinant proteins and peptides.

BACKGROUND OF THE INVENTION

Many peptides and proteins can be produced via recombinant means in a variety of expression systems, e.g., various strains of bacterial, fungal, mammalian or insect cells. However, when bacteria are used as host cells for heterologous gene expression, several problems frequently occur.

For example, heterologous genes encoding small peptides are often poorly expressed in bacteria. Because of their size, most small peptides are unable to adopt stable, soluble conformations and are subject to intracellular degradation by proteases and peptidases present in the host cell. Those small peptides which do manage to accumulate when directly expressed in *E. coli* or other bacterial hosts are usually found in the insoluble or "inclusion body" fraction, an occurrence which renders them almost useless for screening purposes in biological or biochemical assays.

Moreover, even if small peptides are not produced in inclusion bodies, the production of small peptides by recombinant means as candidates for new drugs or enzyme inhibitors encounters further problems. Even small linear peptides can adopt an enormous number of potential structures due to their degrees of conformational freedom. Thus a small peptide can have the 'desired' amino-acid sequence and yet have very low activity in an assay because the 'active' peptide conformation is only one of the many alternative structures adopted in free solution. This presents another difficulty encountered in producing small heterologous peptides recombinantly for effective research and therapeutic use.

Inclusion body formation is also frequently observed when the genes for heterologous proteins are expressed in bacterial cells. These inclusion bodies usually require further manipulations in order to solubilize and refold the heterologous protein, with conditions determined empirically and with uncertainty in each case.

If these additional procedures are not successful, little to no protein retaining bioactivity can be recovered from the host cells. Moreover, these additional processes are often technically difficult and prohibitively expensive for practical production of recombinant proteins for therapeutic, diagnostic or other research uses.

To overcome these problems, the art has employed certain peptides or proteins as fusion "partners" with a desired heterologous peptide or protein to enable the recombinant expression and/or secretion of small peptides or larger proteins as fusion proteins in bacterial expression systems. Among such fusion partners are included lacZ and trpE fusion proteins, maltose-binding protein fusions, and glutathione-S-transferase fusion proteins [See, generally, Current Protocols in Molecular Biology, Vol. 2, suppl. 10, publ. John Wiley and Sons, New York, N.Y., pp. 16.4.1–16.8.1 (1990); and Smith et al, *Gene*, 67:31–40 (1988)]. As another example, U.S. Pat. No. 4,801,536 describes the fusion of a bacterial flagellin protein to a desired protein to enable the production of a heterologous gene in a bacterial cell and its secretion into the culture medium as a fusion protein.

However, often fusions of desired peptides or proteins to other proteins (i.e., as fusion partners) at the amino- or carboxyl- termini of these fusion partner proteins have other potential disadvantages. Experience in *E. coli* has shown that a crucial factor in obtaining high levels of gene expression is the efficiency of translational initiation. Translational initiation in *E. coli* is very sensitive to the nucleotide sequence surrounding the initiating methionine codon of the desired heterologous peptide or protein sequence, although the rules governing this phenomenon are not clear. For this reason, fusions of sequences at the amino-terminus of many fusion partner proteins affects expression levels in an unpredictable manner. In addition there are numerous amino- and carboxy-peptidases in *E. coli* which degrade amino- or carboxyl-terminal peptide extensions to fusion partner proteins so that a number of the known fusion partners have a low success rate for producing stable fusion proteins.

The purification of proteins produced by recombinant expression systems is often a serious challenge. There is a continuing requirement for new and easier methods to produce homogeneous preparations of recombinant proteins, and yet a number of the fusion partners currently used in the art possess no inherent properties that would facilitate the purification process. Therefore, in the art of recombinant expression systems, there remains a need for new compositions and processes for the production and purification of stable, soluble peptides and proteins for use in research, diagnostic and therapeutic applications.

SUMMARY OF THE INVENTION

In one aspect, the present invention provides a fusion sequence comprising a thioredoxin-like protein sequence fused to a selected heterologous peptide or protein. The peptide or protein may be fused to the amino terminus of the thioredoxin-like sequence, the carboxyl terminus of the thioredoxin-like sequence, or within the thioredoxin-like sequence (e.g., within the active-site loop of thioredoxin). The fusion sequence according to this invention may optionally contain a linker peptide between the thioredoxin-like sequence and the selected peptide or protein. This linker provides, where needed, a selected cleavage site or a stretch of amino acids capable of preventing steric hindrance between the thioredoxin-like molecule and the selected peptide or protein.

As another aspect, the present invention provides a DNA molecule encoding the fusion sequence defined above in association with, and under the control of, an expression control sequence capable of directing the expression of the fusion protein in a desired host cell.

Still a further aspect of the invention is a host cell transformed with, or having integrated into its genome, a DNA sequence comprising a thioredoxin-like DNA sequence fused to the DNA sequence of a selected heterologous peptide or protein. This fusion sequence is desirably under the control of an expression control sequence capable of directing the expression of a fusion protein in the cell.

As yet another aspect, there is provided a novel method for increasing the expression of soluble recombinant proteins. The method includes culturing under suitable conditions the above-described host cell to produce the fusion protein.

In one embodiment of this method, if the resulting fusion protein is cytoplasmic, the cell can be lysed by conventional means to obtain the soluble fusion protein. More preferably in the case of cytoplasmic fusion proteins, the method includes releasing the fusion protein from the host cell by applying osmotic shock or freeze/thaw treatments to the cell. In this case the fusion protein is selectively released from the interior of the cell via the zones of adhesion that exist between the inner and outer membranes of *E. coli*. The fusion protein is then purified by conventional means. In still another embodiment, if a secretory leader is employed in the fusion protein construct, the fusion protein can be recovered from a periplasmic extract or from the cell culture medium. As yet a further step in the above methods, the desired protein can be cleaved from fusion with the thioredoxin-like protein by conventional means.

Other aspects and advantages of the present invention will be apparent upon consideration of the following detailed description of preferred embodiments thereof.

SUMMARY OF THE DRAWINGS

FIGS. 1A, 1B, 1C and 1D illustrate the DNA sequence of the expression plasmid pALtrxA/EK-/IL11ΔPro-581 (SEQ ID NO:13) and the amino acid sequence for the fusion protein therein (SEQ ID NO:14), described in Example 1.

FIG. 2 illustrates the DNA sequence (SEQ ID NO:15) and amino acid sequence (SEQ ID NO:16) of the macrophage inhibitory protein-1α (MIP-1α) protein used in the construction of a thioredoxin fusion protein described in Example 3.

FIG. 3 illustrates the DNA sequence (SEQ ID NO:17) and amino acid sequence (SEQ ID NO:18) of the bone morphogenetic protein-2 (BMP-2) protein used in the construction of a thioredoxin fusion protein described in Example 4.

FIG. 4 is a schematic drawing illustrating the insertion of an enterokinase cleavage site into the active-site loop of *E. coli* thioredoxin (trxA) described in Example 5.

FIG. 5 is a schematic drawing illustrating random peptide insertions into the active-site loop of *E. coli* thioredoxin (trxA) described in Example 5.

FIG. 6 and FIG. 6A illustrate the DNA sequence (SEQ ID NO:19) and amino acid sequence (SEQ ID NO:20) of the human interleukin-6 (IL6) protein used in the construction of a thioredoxin fusion protein described in Example 6.

FIG. 7 illustrates the DNA sequence (SEQ ID NO:23) and amino acid sequence (SEQ ID NO:24) of the M-CSF protein used in the construction of a thioredoxin fusion protein described in Example 7.

DETAILED DESCRIPTION OF THE INVENTION

The methods and compositions of the present invention permit the production of large amounts of heterologous peptides or proteins in a stable, soluble form in certain host cells which normally express limited amounts of such peptides or proteins. The present invention produces fusion proteins which retain the desirable characteristics of a thioredoxin-like protein (i.e. stability, solubility and a high level of expression). The invention also allows a small peptide insert into an internal region of the thioredoxin-like sequence (e.g. the active site loop of thioredoxin) to be accessible on the surface of the molecule. These fusion proteins also permit a peptide or protein fused at the free ends of the thioredoxin-like protein to achieve its desired conformation.

According to the present invention, the DNA sequence encoding a heterologous peptide or protein selected for expression in a recombinant system is desirably fused to a thioredoxin-like DNA sequence for expression in the host cell. A thioredoxin-like DNA sequence is defined herein as a DNA sequence encoding a protein or fragment of a protein characterized by an amino acid sequence having at least 18% homology with the amino acid sequence of *E. coli* thioredoxin (SEQ ID NO:22) over an amino acid sequence length of 80 amino acids. Alternatively, a thioredoxin DNA sequence is defined as a DNA sequence encoding a protein or fragment of a protein characterized by a crystalline structure substantially similar to that of human or *E. coli* thioredoxin (SEQ ID NO: 22), e.g. glutaredoxin. The amino acid sequence of *E. coli* thioredoxin is described in H. Eklund et al, *EMBO J.*, 3:1443–1449 (1984). The three-dimensional structure of *E. coli* thioredoxin is depicted in FIG. 2 of A. Holmgren, *J. Biol. Chem.*, 264:13963–13966 (1989). FIG. 1 below nucleotides 2242–2568 contains a DNA sequence encoding the *E. coli* thioredoxin protein [Lim et al, *J. Bacteriol.*, 163:311–316 (1985)] (SEQ ID NO:21). The three latter publications are incorporated herein by reference for the purpose of providing information on thioredoxin which is known to one of skill in the art.

As the primary example of a thioredoxin-like protein useful in this invention, *E. coli* thioredoxin (SEQ ID NO:21 and SEQ ID NO:22) has the following characteristics. *E. coli* thioredoxin is a small protein, only 11.7 kD, and can be expressed to high levels (>10%, corresponding to a concentration of 15 uM if cells are lysed at 10 $A_{550}$/ml). The small size and capacity for high expression of the protein contributes to a high intracellular concentration. *E. coli* thioredoxin is further characterized by a very stable, tight structure which can minimize the effects on overall structural stability caused by fusion to the desired peptide or proteins.

The three dimensional structure of *E. coli* thioredoxin is known and contains several surface loops, including a unique active site loop between residues $Cys_{33}$ and $Cys_{36}$ which protrudes from the body of the protein. This active site loop is an identifiable, accessible surface loop region and is not involved in any interactions with the rest of the protein that contribute to overall structural stability. It is therefore a good candidate as a site for peptide insertions. Both the amino- and carboxyltermini of *E. coli* thioredoxin are on the surface of the protein, and are readily accessible for fusions.

*E. coli* thioredoxin is also stable to proteases. Thus, *E. coli* thioredoxin may be desirable for use in *E. coli* expression systems, because as an *E. coli* protein it is characterized by stability to *E. coli* proteases. *E. coli* thioredoxin is also stable to heat up to 80° C. and to low pH. Other thioredoxin-like proteins encoded by thioredoxin-like DNA sequences useful in this invention may share the homologous amino acid sequences, and similar physical and structural characteristics. Thus, DNA sequences encoding other thioredoxin-like proteins may be used in place of *E. coli* thioredoxin (SEQ ID NO:21 and SEQ ID NO:22) according to this invention. For example, the DNA sequence encoding other species' thioredoxin, e.g., human thioredoxin, may be employed in the compositions and methods of this invention. Both the primary sequence and computer-predicted secondary structures of human and *E. coli* thioredoxins are very similar. Human thioredoxin also carries the same active site loop as is found in the *E. coli* protein. Insertions into the human thioredoxin active site loop and on the amino and carboxyl termini may be as well tolerated as those in *E. coli* thioredoxin.

Other thioredoxin-like sequences which may be employed in this invention include all or portions of the proteins glutaredoxin and various species' homologs thereof [A. Holmgren, cited above]. Although *E. coli* glutaredoxin and *E. coli* thioredoxin share less than 20% amino acid homology, the two proteins do have conformational and functional similarities [Eklund et al, *EMBO J.*, 3:1443–1449 (1984)].

All or a portion of the DNA sequence encoding protein disulfide isomerase (PDI) and various species' homologs thereof [J. E. Edman et al, *Nature*, 317:267–270 (1985)] may also be employed as a thioredoxin-like DNA sequence, since a repeated domain of PDI shares >18% homology with *E. coli* thioredoxin. The two latter publications are incorporated herein by reference for the purpose of providing information on glutaredoxin and PDI which is known and available to one of skill in the art.

Similarly the DNA sequence encoding phosphoinositide-specific phospholipase C (PI-PLC), fragments thereof and various species' homologs thereof [C. F. Bennett et al, *Nature*, 334:268–270 (1988)] may also be employed in the present invention as a thioredoxin-like sequence based on the amino acid sequence homology with *E. coli* thioredoxin. All or a portion of the DNA sequence encoding an endoplasmic reticulum protein, such as ERp72, or various species homologs thereof are also included as thioredoxin-like DNA sequences for the purposes of this invention [R. A. Mazzarella et al, *J. Biol. Chem.*, 265:1094–1101 (1990)] based on amino acid sequence homology. Another thioredoxin-like sequence is a DNA sequence which encodes all or a portion of an adult T-cell leukemia-derived factor (ADF) or other species homologs thereof [N. Wakasugi et al, *Proc. Natl. Acad. Sci., USA*, 87:8282–8286 (1990)] based on amino acid sequence homology to *E. coli* thioredoxin. The three latter publications are incorporated herein by reference for the purpose of providing information on PI-PLC, ERp72, and ADF which are known and available to one of skill in the art.

It is expected from the definition of thioredoxin-like DNA sequence used above that other sequences not specifically identified above, or perhaps not yet identified or published, may be useful as thioredoxin-like sequences based on their amino acid sequence similarities to *E. coli* thioredoxin and characteristic crystalline structural similarities to *E. coli* thioredoxin and the other thioredoxin-like proteins. Based on the above description, one of skill in the art should be able to select and identify, or, if desired, modify, a thioredoxin-like DNA sequence for use in this invention without resort to undue experimentation. For example, simple point mutations made to portions of native thioredoxin or native thioredoxin-like sequences which do not effect the structure of the resulting molecule are alternative thioredoxin-like sequences, as are allelic variants of native thioredoxin or native thioredoxin-like sequences.

DNA sequences which hybridize to the sequence for *E. coli* thioredoxin (SEQ ID NO:21) or its structural homologs under either stringent or relaxed hybridization conditions also encode thioredoxin-like proteins for use in this invention. An example of one such stringent hybridization condition is hybridization at 4XSSC at 65° C., followed by a washing in 0.1XSSC at 65° C. for an hour. Alternatively an exemplary stringent hybridization condition is in 50% formamide, 4XSSC at 42° C. Examples of non-stringent hybridization conditions are 4XSSC at 50° C. or hybridization with 30–40% formamide at 42° C. The use of all such thioredoxin-like sequences are believed to be encompassed in this invention.

Construction of a fusion sequence of the present invention, which comprises the DNA sequence of a selected peptide or protein and the DNA sequence of a thioredoxin-like sequence, employs conventional genetic engineering techniques [see, Sambrook et al, *Molecular Cloning. A Laboratory Manual.*, Cold Spring Harbor Laboratory, Cold Spring Harbor, New York (1989)]. Fusion sequences may be prepared in a number of different ways. For example, the selected heterologous protein may be fused to the amino terminus of the thioredoxin-like molecule. Alternatively, the selected protein sequence may be fused to the carboxyl terminus of the thioredoxin-like molecule. Small peptide sequences could also be fused to either of the above-mentioned positions of the thioredoxin-like sequence to produce them in a structurally unconstrained manner.

This fusion of a desired heterologous peptide or protein to the thioredoxin-like protein increases the stability of the peptide or protein. At either the amino or carboxyl terminus, the desired heterologous peptide or protein is fused in such a manner that the fusion does not destabilize the native structure of either protein. Additionally, fusion to the soluble thioredoxin-like protein improves the solubility of the selected heterologous peptide or protein.

It may be preferred for a variety of reasons that peptides be fused within the active site loop of the thioredoxin-like molecule. The face of thioredoxin surrounding the active site loop has evolved, in keeping with the protein's major function as a nonspecific protein disulfide oxido-reductase, to be able to interact with a wide variety of protein surfaces. The active site loop region is found between segments of strong secondary structure and offers many advantages for peptide fusions.

A small peptide inserted into the active-site loop of a thioredoxin-like protein is present in a region of the protein which is not involved in maintaining tertiary structure. Therefore the structure of such a fusion protein should be stable. Previous work has shown that *E. coli* thioredoxin can be cleaved into two fragments at a position close to the active site loop, and yet the tertiary interactions stabilizing the protein remain.

The active site loop of *E. coli* thioredoxin (SEQ ID NO:22) has the sequence $NH_2$ . . . $Cys_{33}$-Gly-Pro-$Cys_{36}$ . . . COOH. Fusing a selected peptide with a thioredoxin-like protein in the active loop portion of the protein constrains the peptide at both ends, reducing the degrees of conformational freedom of the peptide, and consequently reducing the number of alternative structures taken by the peptide. The inserted peptide is bound at each end by cysteine residues, which may form a disulfide linkage to each other as they do in native thioredoxin and further limit the conformational freedom of the inserted peptide.

Moreover, this invention places the peptide on the surface of the thioredoxin-like protein. Thus the invention provides a distinct advantage for use of the peptides in screening for bioactive peptide conformations and other assays by presenting peptides inserted in the active site loop in this structural context.

Additionally the fusion of a peptide into the loop protects it from the actions of E. coli amino- and carboxyl-peptidases. Further a restriction endonuclease cleavage site RsrII already exists in the portion of the E. coli thioredoxin DNA sequence (SEQ ID NO:21) encoding the loop region at precisely the correct position for a peptide fusion [see FIG. 4]. RsrII recognizes the DNA sequence CGG(A/T)CCG leaving a three nucleotide long 5'-protruding sticky end. DNA bearing the complementary sticky ends will therefore insert at this site in just one orientation.

A fusion sequence of a thioredoxin-like sequence and a desired protein or peptide sequence according to this invention may optionally contain a linker peptide inserted between the thioredoxin-like sequence and the selected heterologous peptide or protein. This linker sequence may encode, if desired, a polypeptide which is selectably cleavable or digestible by conventional chemical or enzymatic methods. For example, the selected cleavage site may be an enzymatic cleavage site. Examples of enzymatic cleavage sites include sites for cleavage by a proteolytic enzyme, such as enterokinase, Factor Xa, trypsin, collagenase, and thrombin. Alternatively, the cleavage site in the linker may be a site capable of being cleaved upon exposure to a selected chemical, e.g., cyanogen bromide, hydroxylamine, or low pH.

Cleavage at the selected cleavage site enables separation of the heterologous protein or peptide from the thioredoxin fusion protein to yield the mature heterologous peptide or protein. The mature peptide or protein may then be obtained in purified form, free from any polypeptide fragment of the thioredoxin-like protein to which it was previously linked. The cleavage site, if inserted into a linker useful in the fusion sequences of this invention, does not limit this invention. Any desired cleavage site, of which many are known in the art, may be used for this purpose.

The optional linker sequence of a fusion sequence of the present invention may serve a purpose other than the provision of a cleavage site. The linker may also be a simple amino acid sequence of a sufficient length to prevent any steric hindrance between the thioredoxin-like molecule and the selected heterologous peptide or protein.

Whether or not such a linker sequence is necessary will depend upon the structural characteristics of the selected heterologous peptide or protein and whether or not the resulting fusion protein is useful without cleavage. For example, where the thioredoxin-like sequence is a human sequence, the fusion protein may itself be useful as a therapeutic without cleavage of the selected protein or peptide therefrom. Alternatively, where the mature protein sequence may be naturally cleaved, no linker may be needed.

In one embodiment therefore, the fusion sequence of this invention contains a thioredoxin-like sequence fused directly at its amino or carboxyl terminal end to the sequence of the selected peptide or protein. The resulting fusion protein is thus a soluble cytoplasmic fusion protein. In another embodiment, the fusion sequence further comprises a linker sequence interposed between the thioredoxin-like sequence and the selected peptide or protein sequence. This fusion protein is also produced as a soluble cytoplasmic protein. Similarly, where the selected peptide sequence is inserted into the active site loop region or elsewhere within the thioredoxin-like sequence, a cytoplasmic fusion protein is produced.

The cytoplasmic fusion protein can be purified by conventional means. Preferably, as a novel aspect of the present invention, several thioredoxin fusion proteins of this invention may be purified by exploiting an unusual property of thioredoxin. The cytoplasm of E. coli is effectively isolated from the external medium by a cell envelope comprising two membranes, inner and outer, separated from each other by a periplasmic space within which lies a rigid peptidoglycan cell wall. The peptidoglycan wall contributes both shape and strength to the cell. At certain locations in the cell envelope there are "gaps" (called variously Bayer patches, Bayer junctions or adhesion sites) in the peptidoglycan wall where the inner and outer membranes appear to meet and perhaps fuse together. See, M. E. Bayer, J. Bacteriol., 93:1104–1112 (1967) and J. Gen. Microbiol., 53:395–404 (1968). Most of the cellular thioredoxin lies loosely associated with the inner surface of the membrane at these adhesion sites and can be quantitatively expelled from the cell through these adhesion sites by a sudden osmotic shock or by a simple freeze/thaw procedure. See C. A. Lunn and V. P. Pigiet, J. Biol. Chem., 257:11424–11430 (1982) and in Thioredoxin and Glutaredoxin Systems: Structure and Function, p165–176, (1986) ed. A. Holmgren et al, Raven Press, New York. To a lesser extent some EF-Tu (elongation factor-Tu) can be expelled in the same way [Jacobson et al, Biochemistry, 15:2297–2302 (1976)], but, with the exception of the periplasmic contents, the vast majority of E. coli proteins cannot be released by these treatments.

Although there have been reports of the release by osmotic shock of a limited number of heterologous proteins produced in the cytoplasm of E. coli [Denefle et al, Gene, 85:499–510 (1989); Joseph-Liauzun et al, Gene, 86:291–295 (1990); Rosenwasser et al, J. Biol. Chem., 265:13066–13073 (1990)], the ability to be so released is a rare and desirable property not shared by the majority of heterologous proteins. Fusion of a heterologous protein to thioredoxin as described by the present invention not only enhances its expression, solubility and stability as described above, but may also provide for its release from the cell by osmotic shock or freeze/thaw treatments, greatly simplifying its purification. The thioredoxin portion of the fusion protein in some cases, e.g., with MIP, directs the fusion protein towards the adhesion sites, from where it can be released to the exterior by these treatments.

In another embodiment the present invention may employ another component, that is, a secretory leader sequence, among which many are known in the art, e.g. leader sequences of phoA, MBP, β-lactamase, operatively linked in frame to the fusion protein of this invention to enable the expression and secretion of the mature fusion protein into the bacterial periplasmic space or culture medium. This leader sequence may be fused to the amino terminus of the thioredoxin-like molecule when the selected peptide or protein sequence is fused to the carboxyl terminus or to an internal site within the thioredoxin-like sequence. An optional linker could also be present when the peptide or protein is fused at the carboxyl terminus. It is expected that this fusion sequence construct when expressed in an appropriate host cell would be expressed as a secreted fusion protein rather than a cytoplasmic fusion protein. However stability, solubility and high expression should characterize fusion proteins produced using any of these alternative embodiments.

This invention is not limited to any specific type of heterologous peptide or protein. A wide variety of heterologous genes or gene fragments are useful in forming the fusion sequences of the present invention. While the compositions and methods of this invention are most useful for peptides or proteins which are not expressed, expressed in inclusion bodies, or expressed in very small amounts in bacterial and yeast hosts, the heterologous peptides or proteins can include any peptide or protein useful for human or veterinary therapy, diagnostic or research applications in any expression system. For example, hormones, cytokines, growth or inhibitory factors, enzymes, modified or wholly synthetic proteins or peptides can be produced according to this invention in bacterial, yeast, mammalian or other eukaryotic cells and expression systems suitable therefor.

In the examples below illustrating this invention, the proteins expressed by this invention include IL-11, MIP-1α (SEQ ID NO:16), IL6 (SEQ ID NO:20), M-CSF (SEQ ID NO:24), a bone inductive factor called BMP-2 (SEQ ID NO:18), and a variety of small peptides of random sequence (SEQ ID NO:1 through SEQ ID NO:12). These proteins include examples of proteins which, when expressed without a thioredoxin fusion partner, are unstable in $E.$ $coli$ or are found in inclusion bodies.

A variety of DNA molecules incorporating the above-described fusion sequences may be constructed for expressing the heterologous peptide or protein according to this invention. At a minimum a desirable DNA sequence according to this invention comprises a fusion sequence described above, in association with, and under the control of, an expression control sequence capable of directing the expression of the fusion protein in a desired host cell. For example, where the host cell is an $E.$ $coli$ strain, the DNA molecule desirably contains a promoter which functions in $E.$ $coli,$ a ribosome binding site, and optionally, a selectable marker gene and an origin of replication if the DNA molecule is extra-chromosomal. Numerous bacterial expression vectors containing these components are known in the art for bacterial expression, and can easily be constructed by standard molecular biology techniques. Similarly known yeast and mammalian cell vectors and vector components may be utilized where the host cell is a yeast cell or a mammalian cell.

The DNA molecules containing the fusion sequences may be further modified to contain different codons to optimize expression in the selected host cell, as is known in the art.

These DNA molecules may additionally contain multiple copies of the thioredoxin-like DNA sequence, with the heterologous protein fused to only one of the DNA sequences, or with the heterologous protein fused to all copies of the thioredoxin-like sequence. It may also be possible to integrate a thioredoxin-like/heterologous peptide or protein-encoding fusion sequence into the chromosome of a selected host to either replace or duplicate a native thioredoxin-like sequence.

Host cells suitable for the present invention are preferably bacterial cells. For example, the various strains of $E.$ $coli$ (e.g., HB101, W3110 and strains used in the following examples) are well-known as host cells in the field of biotechnology. $E.$ $coli$ strain GI724, used in the following examples, has been deposited with a United States microorganism depository as described in detail below. Various strains of $B.$ $subtilis,$ Pseudomonas, and other bacteria may also be employed in this method.

Many strains of yeast and other eukaryotic cells known to those skilled in the art may also be useful as host cells for expression of the polypeptides of the present invention. Similarly known mammalian cells may also be employed in the expression of these fusion proteins.

To produce the fusion protein of this invention, the host cell is either transformed with, or has integrated into its genome, a DNA molecule comprising a thioredoxin-like DNA sequence fused to the DNA sequence of a selected heterologous peptide or protein, desirably under the control of an expression control sequence capable of directing the expression of a fusion protein. The host cell is then cultured under known conditions suitable for fusion protein production. If the fusion protein accumulates in the cytoplasm of the cell it may be released by conventional bacterial cell lysis techniques and purified by conventional procedures including selective precipitations, solubilizations and column chromatographic methods. If a secretory leader is incorporated into the fusion molecule substantial purification is achieved when the fusion protein is secreted into the periplasmic space or the growth medium.

Alternatively, for cytoplasmic thioredoxin fusion proteins, a selective release from the cell may be achieved by osmotic shock or freeze/thaw procedures. Although final purification is still required for most purposes, the initial purity of fusion proteins in preparations resulting from these procedures is superior to that obtained in conventional whole cell lysates, reducing the number of subsequent purification steps required to attain homogeneity. In a typical osmotic shock procedure, the packed cells containing the fusion protein are resuspended on ice in a buffer containing EDTA and having a high osmolarity, usually due to the inclusion of a solute, such as 20% w/v sucrose, in the buffer which cannot readily cross the cytoplasmic membrane. During a brief incubation on ice the cells plasmolyze as water leaves the cytoplasm down the osmotic gradient. The cells are then switched into a buffer of low osmolarity, and during the osmotic re-equilibration both the contents of the periplasm and proteins localized at the Bayer patches are released to the exterior. A simple centrifugation following this release removes the majority of bacterial cell-derived contaminants from the fusion protein preparation. Alternatively, in a freeze/thaw procedure the packed cells containing the fusion protein are first resuspended in a buffer containing EDTA and are then frozen. Fusion protein release is subsequently achieved by allowing the frozen cell suspension to thaw. The majority of contaminants can be removed as described above by a centrifugation step. The fusion protein is further purified by well-known conventional methods.

These treatments typically release at least 30% of the fusion proteins without lysing the cell cultures. The success of these procedures in releasing significant amounts of several thioredoxin fusion proteins is surprising, since such techniques are not generally successful with a wide range of proteins. The ability of these fusion proteins to be substantially purified by such treatments, which are significantly simpler and less expensive than the purification methods required by other fusion protein systems, may provide the fusion proteins of the invention with a significant advantage over other systems which are used to produce proteins in *E. coli*.

The resulting fusion protein is stable and soluble, often with the heterologous peptide or protein retaining its bioactivity. The heterologous peptide or protein may optionally be separated from the thioredoxin-like protein by cleavage, as discussed above.

In the specific and illustrative embodiments of the compositions and methods of this invention, the *E. coli* thioredoxin (trxA) gene (SEQ ID NO:21) has been cloned and placed in an *E. coli* expression system. An expression plasmid pALtrxA-781 was constructed. This plasmid containing modified IL-11 fused to the thioredoxin sequence and called pALtrxA/EK/IL11ΔPro-581 (SEQ ID NO:13 and SEQ ID NO:14) is described below in Example 1 and in FIG. 1. A modified version of this plasmid containing a different ribosome binding site was employed in the other examples and is specifically described in Example 3. Other conventional vectors may be employed in this invention. The invention is not limited to the plasmids described in these examples.

Plasmid pALtrxA-781 (without the modified IL-11) directs the accumulation of >10% of the total cell protein as thioredoxin in *E. coli* host strain GI724. Examples 2 through 6 describe the use of this plasmid to form and express thioredoxin fusion proteins with BMP-2 (SEQ ID NO:18), IL6 (SEQ ID NO:20) and MIP-1α (SEQ ID NO:16), which are polypeptides.

As an example of the expression of small peptides inserted into the active-site loop, a derivative of pALtrxA-781 has been constructed in which a 13 amino-acid linker peptide sequence containing a cleavage site for the specific protease enterokinase [Leipnieks and Light, *J. Biol. Chem.*, 254:1077-1083 (1979)] has been fused into the active site loop of thioredoxin. This plasmid (pALtrxA-EK) directs the accumulation of >10% of the total cell protein as the fusion protein. The fusion protein is all soluble, indicating that it has probably adopted a 'native' tertiary structure. It is equally as stable as wild type thioredoxin to prolonged incubations at 80° C., suggesting that the strong tertiary structure of thioredoxin has not been compromised by the insertion into the active site loop. The fusion protein is specifically cleaved by enterokinase, whereas thioredoxin is not, indicating that the peptide inserted into the active site loop is present on the surface of the fusion protein.

As described in more detail in Example 5 below, fusions of small peptides (SEQ ID NO:1 through SEQ ID NO:12) were made into the active site loop of thioredoxin. The inserted peptides were 14 residues long and were of totally random composition to test the ability of the system to deal with hydrophobic, hydrophilic and neutral sequences.

The methods and compositions of this invention permit the production of proteins and peptides useful in research, diagnostic and therapeutic fields. The production of fusion proteins according to this invention has a number of advantages. As one example, the production of a selected protein by the present invention as a carboxyl-terminal fusion to *E. coli* thioredoxin (SEQ ID NO:21), or another thioredoxin-like protein, enables avoidance of translation initiation problems often encountered in the production of eukaryotic proteins in *E. coli*. Additionally the initiator methionine usually remaining on the amino-terminus of the heterologous protein is not present and does not have to be removed when the heterologous protein is made as a carboxyl terminal thioredoxin fusion.

The production of fusion proteins according to this invention reliably improves solubility of desired heterologous proteins and enhances their stability to proteases in the expression system. This invention also enables high level expression of certain desirable therapeutic proteins, e.g., IL-11, which are otherwise produced at low levels in bacterial host cells.

This invention may also confer heat stability to the fusion protein, especially if the heterologous protein itself is heat stable. Because thioredoxin, and presumably all thioredoxin-like proteins are heat stable up to 80° C., the present invention may enable the use of a simple heat treatment as an initial effective purification step for some thioredoxin fusion proteins.

In addition to providing high levels of the selected heterologous proteins or peptides upon cleavage from the fusion protein for therapeutic or other uses, the fusion proteins or fusion peptides of the present invention may themselves be useful as therapeutics provided the thioredoxin-like protein is not antigenic to the animal being treated. Further the thioredoxin-like fusion proteins may provide a vehicle for the delivery of bioactive peptides. As one example, human thioredoxin would not be antigenic in humans, and therefore a fusion protein of the present invention with human thioredoxin may be useful as a vehicle for delivering to humans the biologically active peptide to which it is fused. Because human thioredoxin is an intracellular protein, human thioredoxin fusion proteins may be produced in an *E. coli* intracellular expression system. Thus this invention also provides a method for delivering biologically active peptides or proteins to a patient in the form of a fusion protein with an acceptable thioredoxin-like protein.

The present invention also provides methods and reagents for screening libraries of random peptides for their potential enzyme inhibitory, hormone/growth factor agonist and hormone/growth factor antagonist activity. Also provided are methods and reagents for the mapping of known protein sequences for regions of potential interest, including receptor binding sites, substrate binding sites, phosphorylation/modification sites, protease cleavage sites, and epitopes.

Bacterial colonies expressing thioredoxin-like/random peptide fusion proteins may be screened using radiolabelled proteins such as hormones or growth factors as probes. Positives arising from this type of screen would identify mimics of receptor binding sites and may lead to the design of compounds with therapeutic uses. Bacterial colonies expressing thioredoxin-like random peptide fusion proteins may also be screened using antibodies raised against native, active hormones or growth factors. Positives arising from this type of screen could be mimics of surface epitopes present on the original antigen. Where such surface epitopes are responsible for receptor binding, the 'positive' fusion proteins would have biological activity.

Additionally, the thioredoxin-like fusion proteins or fusion peptides of this invention may also be employed to develop monoclonal and polyclonal antibodies, or recombinant antibodies or chimeric antibodies, generated by known methods for diagnostic, purification or therapeutic use. Studies of thioredoxin-like molecules indicate a possible B cell/T cell growth factor activity [N. Wakasuki et al, cited above], which may enhance immune response. The fusion proteins or peptides of the present invention may be employed as antigens to elicit desirable antibodies, which themselves may be further manipulated by known techniques into monoclonal or recombinant antibodies.

Alternatively, antibodies elicited to thioredoxin-like sequences may also be useful in the purification of many different thioredoxin fusion proteins.

The following examples illustrate embodiments of the present invention, but are not intended to limit the scope of the disclosure.

EXAMPLE 1—THIOREDOXIN-IL11 FUSION MOLECULE

A thioredoxin-like fusion molecule of the present invention was prepared using *E. coli* thioredoxin as the thioredoxin-like sequence and recombinant IL-11 [Paul et al, *Proc. Natl. Acad. Sci. U.S.A.*, 87:7512-7516 (1990); see also, copending U.S. patent application Ser. No. 07/526,474, and Ser. No. 07/441,100 and PCT Patent publication WO91/0749, published May 30, 1991 incorporated herein by reference] as the selected heterologous protein. The *E. coli* thioredoxin (trxA) gene (SEQ ID NO:21) was cloned based on its published sequence and employed to construct various related *E. coli* expression plasmids using standard DNA manipulation techniques, described extensively by Sambrook, Fritsch and Maniatis, *Molecular Cloning. A Laboratory Manual*, 2nd edition, Cold Spring Harbor Laboratory, Cold Spring Harbor, N.Y. (1989).

A first expression plasmid pALtrxA-781 was constructed containing the *E. coli* trxA gene without fusion to another sequence. This plasmid further contained sequences which are described in detail below for the related IL-11 fusion plasmid. This first plasmid, which directs the accumulation of >10% of the total cell protein as thioredoxin in an *E. coli* host strain GI724, was further manipulated as described below for the construction of a trxA/IL-11 fusion sequence.

The entire sequence of the related plasmid expression vector, pALtrxA/EK/IL11ΔPro-581 (SEQ ID NO:13 and SEQ ID NO:14), is illustrated in FIG. 1 and contains the following principal features:

Nucleotides 1-2060 contain DNA sequences originating from the plasmid pUC-18 [Norrander et al, *Gene*, 26: 101-106 (1983)] including sequences containing the gene for β-lactamase which confers resistance to the antibiotic ampicillin in host *E. coli* strains, and a colE1-derived origin of replication. Nucleotides 2061-2221 contain DNA sequences for the major leftward promoter (pL) of bacteriophage λ [Sanger et al, *J. Mol. Biol.*, 162:729-773 (1982)], including three operator sequences, $O_L1$, $O_L2$ and $O_L3$. The operators are the binding sites for λcI repressor protein, intracellular levels of which control the amount of transcription initiation from pL. Nucleotides 2222-2241 contain a strong ribosome binding sequence derived from that of gene 10 of bacteriophage T7 [Dunn and Studier *J. Mol. Biol.*, 166:477-535 (1983)].

Nucleotides 2242-2568 contain a DNA sequence encoding the *E. coli* thioredoxin protein (SEQ ID NO:21) [Lim et al, *J. Bacteriol.*, 163:311-316 (1985)]. There is no translation termination codon at the end of the thioredoxin coding sequence in this plasmid.

Nucleotides 2569-2583 contain DNA sequence encoding the amino acid sequence for a short, hydrophilic, flexible spacer peptide "——GSGSG——". Nucleotides 2584-2598 provide DNA sequence encoding the amino acid sequence for the cleavage recognition site of enterokinase (EC 3.4.4.8), "——DDDDK——" [Maroux et al, *J. Biol. Chem.*, 246:5031-5039 (1971)].

Nucleotides 2599-3132 contain DNA sequence encoding the amino acid sequence of a modified form of mature human IL11 [Paul et al, *Proc. Natl. Acad. Sci. USA*, 87:7512-7516 (1990)], deleted for the N-terminal prolyl-residue normally found in the natural protein. The sequence includes a translation termination codon at the 3'-end of the IL11 sequence.

Nucleotides 3133-3159 provide a "Linker" DNA sequence containing restriction endonuclease sites. Nucleotides 3160-3232 provide a transcription termination sequence based on that of the *E. coli* aspA gene [Takagi et al, *Nucl. Acids Res.*, 13:2063-2074 (1985)]. Nucleotides 3233-3632 are DNA sequences derived from pUC-18.

As described in Example 2 below, when cultured under the appropriate conditions in a suitable *E. coli* host strain, this plasmid vector can direct the production of high levels (approximately 10% of the total cellular protein) of a thioredoxin-IL11 fusion protein. By contrast, when not fused to thioredoxin, IL11 accumulated to only 0.2% of the total cellular protein when expressed in an analogous host/vector system.

EXAMPLE 2—EXPRESSION OF A FUSION PROTEIN

A thioredoxin-IL11 fusion protein was produced according to the following protocol using the plasmid constructed as described in Example 1. pALtrxA/EK/IL11ΔPro-581 (SEQ ID NO:13) was transformed into the *E. coli* host strain GI724 (F−, lacI$^q$, lacP$^{L8}$, ampC::-λcI+) by the procedure of Dagert and Ehrlich, *Gene*, 6: 23 (1979). The untransformed host strain *E. coli* GI724 was deposited with the American Type Culture Collection, 12301 Parklawn Drive, Rockville, Md. on Jan. 31, 1991 under ATCC No. 55151 for patent purposes pursuant to applicable laws and regulations. Transformants were selected on 1.5% w/v agar plates containing IMC medium, which is composed of M9 medium [Miller, "Experiments in Molecular Genetics", Cold Spring Harbor Laboratory, New York (1972)] supplemented with 0.5% w/v glucose, 0.2% w/v casamino acids and 100 μg/ml ampicillin.

GI724 contains a copy of the wild-type λcI repressor gene stably integrated into the chromosome at the ampC locus, where it has been placed under the transcriptional control of *Salmonella typhimurium* trp promoter/operator sequences. In GI724, λcI protein is made only during growth in tryptophan-free media, such as minimal media or a minimal medium supplemented with casamino acids such as IMC, described above. Addition of tryptophan to a culture of GI724 will repress the trp promoter and turn off synthesis of λcI, gradually causing the induction of transcription from pL promoters if they are present in the cell.

GI724 transformed with pALtrxA/EK/IL11ΔPro-581 (SEQ ID NO:13 and SEQ ID NO:14) was grown at 37° C. to an $A_{550}$ of 0.5 in IMC medium. Tryptophan was added to a final concentration of 100 μg/ml and the culture incubated for a further 4 hours. During this time thioredoxin-IL11 fusion protein accumulated to approximately 10% of the total cell protein.

All of the fusion protein was found to be in the soluble cellular fraction, and was purified as follows. Cells were lysed in a french pressure cell at 20,000 psi in 50 mM HEPES pH 8.0, 1 mM phenylmethylsulfonyl fluoride. The lysate was clarified by centrifugation at 15,000×g for 30 minutes and the supernatant loaded onto a QAE-Toyopearl column. The flow-through fractions were discarded and the fusion protein eluted with 50 mM HEPES pH 8.0, 100 mM NaCl. The eluate was adjusted to 2M NaCl and loaded onto a column of phenyl-Toyopearl. The flow-through fractions were again discarded and the fusion protein eluted with 50 mM HEPES pH 8.0, 0.5M NaCl.

The fusion protein was then dialyzed against 25 mM HEPES pH 8.0 and was >80% pure at this stage. By T1165 bioassay [Paul et al, cited above] the purified thioredoxin-IL11 protein exhibited an activity of $8 \times 10^5$ U/mg. This value agrees closely on a molar basis with the activity of $2 \times 10^6$ U/mg found for COS cell-derived IL11 in the same assay. One milligram of the fusion protein was cleaved at 37° C. for 20 hours with 1000 units of bovine enterokinase [Leipnieks and Light, *J. Biol. Chem.*, 254:1677–1683 (1979)] in 1 ml 10mM Tris-Cl (pH8.0)/10 mM $CaCl_2$. IL11 could be recovered from the reaction products by passing them over a QAE-Toyopearl column in 25 mM HEPES pH 8.0, where IL11 was found in the flow-through fractions. Uncleaved fusion protein, thioredoxin and enterokinase remained bound on the column.

The IL11 prepared in this manner had a bioactivity in the T1165 assay of $2.5 \times 10^6$ U/mg.

EXAMPLE 3—THIOREDOXIN-MIP FUSION MOLECULE

Human macrophage inflammatory protein 1α (MIP-1α) (SEQ ID NO:16) can be expressed at high levels in *E. coli* as a thioredoxin fusion protein using an expression vector similar to pALtrxA/EK/IL11ΔPro-581 described in Example 1 above but modified in the following manner to replace the ribosome binding site of bacteriophage T7 with that of λCII. In the plasmid of Example 1, nucleotides 2222 and 2241 were removed by conventional means. Inserted in place of those nucleotides was a sequence of nucleotides formed by nucleotides 35566 to 35472 and 38137 to 38361 from bacteriophage lambda as described in Sanger et al (1982) cited above. This reference is incorporated by reference for the purpose of disclosing this sequence. To express a thioredoxin-MIP-1α fusion the DNA sequence in the thusly-modified pALtrxA/EK/IL11ΔPro-581 encoding human IL11 (nucleotides 2599-3132) is replaced by the 213 nucleotide DNA sequence (SEQ ID NO:15) shown in FIG. 2 encoding full-length, mature human MIP-1α [Nakao et al, *Mol. Cell. Biol.*, 10:3646–3658 (1990)].

The host strain and expression protocol used for the production of thioredoxin-MIP-1α fusion protein are as described in Example 1. As was seen with the thioredoxin-IL11 fusion protein, all of the thioredoxin-MIP-1α fusion protein was found in the soluble cellular fraction, representing up to 20% of the total protein.

Cells were lysed as in Example 1 to give a protein concentration in the crude lysate of 10 mg/ml. This lysate was then heated at 80° C. for 10 min to precipitate the majority of contaminating *E. coli* proteins and was clarified by centrifugation at 130,000×g for 60 minutes. The pellet was discarded and the supernatant loaded onto a Mono Q column. The fusion protein eluted at approximately 0.5M NaCl from this column and was >80% pure at this stage. After dialysis to remove salt the fusion protein could be cleaved by an enterokinase treatment as described in Example 1 to release MIP-1α.

EXAMPLE 4—THIOREDOXIN-BMP2 FUSION MOLECULE

Human Bone Morphogenetic Protein 2 (BMP-2) can be expressed at high levels in *E. coli* as a thioredoxin fusion protein using the modified expression vector described in Example 3. The DNA sequence encoding human IL11 in the modified pALtrxA/EK/IL11ΔPro-581 (nucleotides 2599-3132) is replaced by the 345 nucleotide DNA sequence (SEQ ID NO:17) shown in FIG. 3 encoding full-length, mature human BMP-2 [Wozney et al, *Science*, 242:1528–1534 (1988)].

In this case the thioredoxin-BMP-2 fusion protein appeared in the insoluble cellular fraction when strain GI724 containing the expression vector was grown in medium containing tryptophan at 37° C. However, when the temperature of the growth medium was lowered to 20° C. the fusion protein was found in the soluble cellular fraction.

EXAMPLE 5—THIOREDOXIN-SMALL PEPTIDE FUSION MOLECULES

Native *E. coli* thioredoxin can be expressed at high levels in *E. coli* using strain GI724 containing the same plasmid expression vector described in Example 3 deleted for nucleotides 2569-3129, and employing the growth and induction protocol outlined in Example 1. Under these conditions thioredoxin accumulated to approximately 10% of the total protein, all of it in the soluble cellular fraction.

FIG. 4 illustrates insertion of 13 amino acid residues encoding an enterokinase cleavage site into the active site loop of thioredoxin, between residues $G_{34}$ and $P_{35}$ of the thioredoxin protein sequence. The fusion protein containing this internal enterokinase site was expressed at levels equivalent to native thioredoxin, and was cleaved with an enterokinase treatment as outlined in Example 1 above. The fusion protein was found to be as stable as native thioredoxin to heat treatments, being resistant to a 10 minute incubation at 80° C. as described in Example 4.

Below are listed twelve additional peptide insertions which were also made into the active site loop of thioredoxin between $G_{34}$ and $P_{35}$. The sequences are each 14 amino acid residues in length and are random in composition. Each of the thioredoxin fusion proteins containing these random insertions were made at levels comparable to native thioredoxin. All of them were found in the soluble cellular fraction. These peptides include the following sequences:

Pro-Leu-Gln-Arg-Ile-Pro-Pro-Gln-Ala-Leu-Arg-Val-Glu-Gly (SEQ ID NO:1),
Pro-Arg-Asp-Cys-Val-Gln-Arg-Gly-Lys-Ser-Leu-Ser-Leu-Gly (SEQ ID NO:2),
Pro-Met-Arg-His-Asp-Val-Arg-Cys-Val-Leu-His-Gly-Thr-Gly (SEQ ID NO:3),
Pro-Gly-Val-Arg-Leu-Pro-Ile-Cys-Tyr-Asp-Asp-Ile-Arg-Gly (SEQ ID NO:4),
Pro-Lys-Phe-Ser-Asp-Gly-Ala-Gln-Gly-Leu-Gly-Ala-Val-Gly (SEQ ID NO:5),
Pro-Pro-Ser-Leu-Val-Gln-Asp-Asp-Ser-Phe-Glu-Asp-Arg-Gly (SEQ ID NO:6),
Pro-Trp-Ile-Asn-Gly-Ala-Thr-Pro-Val-Lys-Ser-Ser-Ser-Gly (SEQ ID NO:7),

Pro-Ala-His-Arg-Phe-Arg-Gly-Gly-Ser-Pro-Ala-Ile-Phe-Gly (SEQ ID NO:8),
Pro-Ile-Met-Gly-Ala-Ser-His-Gly-Glu-Arg-Gly-Pro-Glu-Gly (SEQ ID NO:9),
Pro-Asp-Ser-Leu-Arg-Arg-Arg-Glu-Gly-Phe-Gly-Leu-Leu-Gly (SEQ ID NO:10),
Pro-Ser-Glu-Tyr-Pro-Gly-Leu-Ala-Thr-Gly-His-His-Val-Gly (SEQ ID NO: 11), and
Pro-Leu-Gly-Val-Leu-Gly-Ser-Ile-Trp-Leu-Glu-Arg-Gln-Gly (SEQ ID NO:12).

The inserted sequences contained examples that were both hydrophobic and hydrophilic, and examples that contained cysteine residues. It appears that the active-site loop of thioredoxin can tolerate a wide variety of peptide insertions resulting in soluble fusion proteins. Standard procedures can be used to purify these loop "inserts".

EXAMPLE 6—HUMAN INTERLEUKIN-6

Human interleukin-6 (IL-6) can be expressed at high levels in *E. coli* as a thioredoxin fusion protein using an expression vector similar to modified pALtrxA/EK-/IL11ΔPro-581 described in Example 3 above. To express a thioredoxin-IL6 fusion the DNA sequence in modified pALtrxA/EK/IL11αPro-581 encoding human IL11 (nucleotides 2599–3132) is replaced by the 561 nucleotide DNA sequence (SEQ ID NO:19) shown in FIG. 6 encoding full-length, mature human IL6 [Hirano et al, *Nature*, 324:73–76 (1986)]. The host strain and expression protocol used for the production of thioredoxin-IL6 fusion protein are as described in Example 1.

When the fusion protein was synthesized at 37° C., approximately 50% of it was found in the "inclusion body" or insoluble fraction. However all of the thioredoxin-IL6 fusion protein, representing up to 10% of the total cellular protein, was found in the soluble fraction when the temperature of synthesis was lowered to 25° C.

EXAMPLE 7—HUMAN MACROPHAGE COLONY STIMULATING FACTOR

Human Macrophage Colony Stimulating Factor (M-CSF) can be expressed at high levels in *E. coli* as a thioredoxin fusion protein using the modified expression vector similar to pALtrxA/EK/IL11ΔPro-581 described in Example 3 above.

The DNA sequence encoding human IL11 in modified pALtrxA/EK/IL11ΔPro-581 (nucleotides 2599–3135) is replaced by the 669 nucleotide DNA sequence shown in FIG. 7 encoding the first 223 amino acids of mature human M-CSFβ [G. G. Wong et al, *Science*, 235:1504–1508 (1987)]. The host strain and expression protocol used for the production of thioredoxin-MCSF fusion protein was as described in Example 2 above.

As was seen with the thioredoxin-IL11 fusion protein, all of the thioredoxin-MCSF fusion protein was found in the soluble cellular fraction, representing up to 10% of the total protein.

EXAMPLE 8—RELEASE OF FUSION PROTEIN VIA OSMOTIC SHOCK

To determine whether or not the fusions of heterologous proteins to thioredoxin according to this invention enable targeting to the host cell's adhesion sites and permit the release of the fusion proteins from the cell, the cells were exposed to simple osmotic shock and freeze/thaw procedures.

Cells overproducing wild-type *E. coli* thioredoxin, human thioredoxin, the *E. coli* thioredoxin-MIP1α fusion or the *E. coli* thioredoxin-IL11 fusion were used in the following procedures.

For an osmotic shock treatment, cells were resuspended at 2 $A_{550}$/ml in 20 mM Tris-Cl pH 8.0/2.5 mM EDTA/20% w/v sucrose and kept cold on ice for 10 minutes. The cells were then pelleted by centrifugation (12,000×g, 30 seconds) and gently resuspended in the same buffer as above but with sucrose omitted. After an additional 10 minute period on ice, to allow for the osmotic release of proteins, cells were re-pelleted by centrifugation (12,000×g, 2 minutes) and the supernatant ("shockate") examined for its protein content. Wild-type *E. coli* thioredoxin and human thioredoxin were quantitatively released, giving "shockate" preparations which were >80% pure thioredoxin. More significantly >80% of the thioredoxin-MIP1α and >50% of the thioredoxin-IL11 fusion proteins were released by this osmotic treatment.

A simple freeze/thaw procedure produced similar results, releasing thioredoxin fusion proteins selectively, while leaving most of the other cellular proteins inside the cell. A typical freeze/thaw procedure entails resuspending cells at 2 $A_{550}$/ml in 20 mM Tris-Cl pH 8.0/2.5 mM EDTA and quickly freezing the suspension in dry ice or liquid nitrogen. The frozen suspension is then allowed to slowly thaw before spinning out the cells (12,000×g, 2 minutes) and examining the supernatant for protein.

Although the resultant "shockate" may require additional purification, the initial "shockate" is characterized by the absence of nucleic acid contaminants. Thus, compared to an initial lysate, the purity of the "shockate" is significantly better, and does not require the difficult removal of DNA from bacterial lysates. Fewer additional steps should be required for total purity of the "shockate".

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

---

SEQUENCE LISTING ( 1 ) GENERAL INFORMATION:

( i i i ) NUMBER OF SEQUENCES: 24

( 2 ) INFORMATION FOR SEQ ID NO:1:

-continued (i) SEQUENCE CHARACTERISTICS:
    (A) LENGTH: 14 amino acids
    (B) TYPE: amino acid
    (D) TOPOLOGY: unknown (ii) MOLECULE TYPE: peptide (xi) SEQUENCE DESCRIPTION: SEQ ID NO:1:

```
Pro Leu Gln Arg Ile Pro Pro Gln Ala Leu Arg Val Glu Gly
1               5                   10
```

(2) INFORMATION FOR SEQ ID NO:2:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:2:

```
Pro Arg Asp Cys Val Gln Arg Gly Lys Ser Leu Ser Leu Gly
1               5                   10
```

(2) INFORMATION FOR SEQ ID NO:3:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:3:

```
Pro Met Arg His Asp Val Arg Cys Val Leu His Gly Thr Gly
1               5                   10
```

(2) INFORMATION FOR SEQ ID NO:4:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:4:

```
Pro Gly Val Arg Leu Pro Ile Cys Tyr Asp Asp Ile Arg Gly
1               5                   10
```

(2) INFORMATION FOR SEQ ID NO:5:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:5:

```
Pro Lys Phe Ser Asp Gly Ala Gln Gly Leu Gly Ala Val Gly
1               5                   10
```

(2) INFORMATION FOR SEQ ID NO:6:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide ( x i ) SEQUENCE DESCRIPTION: SEQ ID NO:6:

Pro Pro Ser Leu Val Gln Asp Asp Ser Phe Gly Asp Arg Gly
1               5                           10

( 2 ) INFORMATION FOR SEQ ID NO:7:

( i ) SEQUENCE CHARACTERISTICS:
    ( A ) LENGTH: 14 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:7:

Pro Trp Ile Asn Gly Ala Thr Pro Val Lys Ser Ser Ser Gly
1               5                           10

( 2 ) INFORMATION FOR SEQ ID NO:8:

( i ) SEQUENCE CHARACTERISTICS:
    ( A ) LENGTH: 14 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:8:

Pro Ala His Arg Phe Arg Gly Gly Ser Pro Ala Ile Phe Gly
1               5                           10

( 2 ) INFORMATION FOR SEQ ID NO:9:

( i ) SEQUENCE CHARACTERISTICS:
    ( A ) LENGTH: 14 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:9:

Pro Ile Met Gly Ala Ser His Gly Glu Arg Gly Pro Glu Gly
1               5                           10

( 2 ) INFORMATION FOR SEQ ID NO:10:

( i ) SEQUENCE CHARACTERISTICS:
    ( A ) LENGTH: 14 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:10:

Pro Asp Ser Leu Arg Arg Arg Glu Gly Phe Gly Leu Leu Gly
1               5                           10

( 2 ) INFORMATION FOR SEQ ID NO:11:

( i ) SEQUENCE CHARACTERISTICS:
    ( A ) LENGTH: 14 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:11:

Pro Ser Glu Tyr Pro Gly Leu Ala Thr Gly His His Val Gly
1               5                           10

( 2 ) INFORMATION FOR SEQ ID NO:12:

( i ) SEQUENCE CHARACTERISTICS:
    ( A ) LENGTH: 14 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:12:

Pro Leu Gly Val Leu Gly Ser Ile Trp Leu Glu Arg Gln Gly
1               5                   10

( 2 ) INFORMATION FOR SEQ ID NO:13:

( i ) SEQUENCE CHARACTERISTICS:
    ( A ) LENGTH: 3632 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: CDS
    ( B ) LOCATION: 2242..3132

( i x ) FEATURE:
    ( A ) NAME/KEY: miscfeature
    ( B ) LOCATION: 2242..2568
    ( D ) OTHER INFORMATION: /product="E. coli thioredoxin
            protein"
            / note="Lim et al, J. Bacteriol., 163:311-316

( i x ) FEATURE:
    ( A ) NAME/KEY: RBS
    ( B ) LOCATION: 2222..2241
    ( D ) OTHER INFORMATION: /standardname="ribosome binding
            sequence"
            / note="Dunn and Studier, J. Mol. Biol, ( i x ) FEATURE:
    ( A ) NAME/KEY: miscfeature
    ( B ) LOCATION: 2061..2221
    ( D ) OTHER INFORMATION: /function="leftward promoter of
            bacteriophage lambda"
            / note="Sanger et al, J. Mol. Biol, 162:729-773

( i x ) FEATURE:
    ( A ) NAME/KEY: miscfeature
    ( B ) LOCATION: 1..2060
    ( D ) OTHER INFORMATION: /function="derived from plasmid
            pUC-18"

( i x ) FEATURE:
    ( A ) NAME/KEY: miscfeature
    ( B ) LOCATION: 2569..2583
    ( D ) OTHER INFORMATION: /function="short, hydrophilic
            flexible spacer peptide"

( i x ) FEATURE:
    ( A ) NAME/KEY: miscfeature
    ( B ) LOCATION: 2584..2598
    ( D ) OTHER INFORMATION: /function="enterokinase cleavage
            recognition site"
            / note="Maroux et al, J. Biol. Chem., ( i x ) FEATURE:
    ( A ) NAME/KEY: miscfeature
    ( B ) LOCATION: 2599..3132
    ( D ) OTHER INFORMATION: /product="nodified form of mature
            human IL11"
            / note="Paul et al, Proc. Natl. Acad. Sci. USA, ( i x ) FEATURE:
    ( A ) NAME/KEY: miscfeature
    ( B ) LOCATION: 3133..3159
    ( D ) OTHER INFORMATION: /function="linker sequence
            containing restriction endonuclease sites"

( i x ) FEATURE:

(A) NAME/KEY: miscfeature
(B) LOCATION: 3160..3232
(D) OTHER INFORMATION: /function="transcription termination sequence based on E. coli aspA"
/ note="Takagi et al, Nucl. Acids Res., (ix) FEATURE:
(A) NAME/KEY: miscfeature
(B) LOCATION: 3233..3632
(D) OTHER INFORMATION: /function="DNA sequences derived from pUC-18"

(xi) SEQUENCE DESCRIPTION: SEQ ID NO:13:

| | | | | | |
|---|---|---|---|---|---|
| GACGAAAGGG | CCTCGTGATA | CGCCTATTTT | TATAGGTTAA | TGTCATGATA | ATAATGGTTT | 60 |
| CTTAGACGTC | AGGTGGCACT | TTTCGGGGAA | ATGTGCGCGG | AACCCCTATT | TGTTTATTTT | 120 |
| TCTAAATACA | TTCAAATATG | TATCCGCTCA | TGAGACAATA | ACCCTGATAA | ATGCTTCAAT | 180 |
| AATATTGAAA | AAGGAAGAGT | ATGAGTATTC | AACATTTCCG | TGTCGCCCTT | ATTCCCTTTT | 240 |
| TTGCGGCATT | TTGCCTTCCT | GTTTTGCTC | ACCCAGAAAC | GCTGGTGAAA | GTAAAAGATG | 300 |
| CTGAAGATCA | GTTGGGTGCA | CGAGTGGGTT | ACATCGAACT | GGATCTCAAC | AGCGGTAAGA | 360 |
| TCCTTGAGAG | TTTTCGCCCC | GAAGAACGTT | TTCCAATGAT | GAGCACTTTT | AAAGTTCTGC | 420 |
| TATGTGGCGC | GGTATTATCC | CGTATTGACG | CCGGGCAAGA | GCAACTCGGT | CGCCGCATAC | 480 |
| ACTATTCTCA | GAATGACTTG | GTTGAGTACT | CACCAGTCAC | AGAAAAGCAT | CTTACGGATG | 540 |
| GCATGACAGT | AAGAGAATTA | TGCAGTGCTG | CCATAACCAT | GAGTGATAAC | ACTGCGGCCA | 600 |
| ACTTACTTCT | GACAACGATC | GGAGGACCGA | AGGAGCTAAC | CGCTTTTTTG | CACAACATGG | 660 |
| GGGATCATGT | AACTCGCCTT | GATCGTTGGG | AACCGGAGCT | GAATGAAGCC | ATACCAAACG | 720 |
| ACGAGCGTGA | CACCACGATG | CCTGTAGCAA | TGGCAACAAC | GTTGCGCAAA | CTATTAACTG | 780 |
| GCGAACTACT | TACTCTAGCT | TCCCGGCAAC | AATTAATAGA | CTGGATGGAG | GCGGATAAAG | 840 |
| TTGCAGGACC | ACTTCTGCGC | TCGGCCCTTC | CGGCTGGCTG | GTTTATTGCT | GATAAATCTG | 900 |
| GAGCCGGTGA | GCGTGGGTCT | CGCGGTATCA | TTGCAGCACT | GGGGCCAGAT | GGTAAGCCCT | 960 |
| CCCGTATCGT | AGTTATCTAC | ACGACGGGGA | GTCAGGCAAC | TATGGATGAA | CGAAATAGAC | 1020 |
| AGATCGCTGA | GATAGGTGCC | TCACTGATTA | AGCATTGGTA | ACTGTCAGAC | CAAGTTTACT | 1080 |
| CATATATACT | TTAGATTGAT | TTAAAACTTC | ATTTTTAATT | TAAAAGGATC | TAGGTGAAGA | 1140 |
| TCCTTTTTGA | TAATCTCATG | ACCAAAATCC | CTTAACGTGA | GTTTTCGTTC | CACTGAGCGT | 1200 |
| CAGACCCCGT | AGAAAAGATC | AAAGGATCTT | CTTGAGATCC | TTTTTTTCTG | CGCGTAATCT | 1260 |
| GCTGCTTGCA | AACAAAAAAA | CCACCGCTAC | CAGCGGTGGT | TTGTTGCCG | GATCAAGAGC | 1320 |
| TACCAACTCT | TTTTCCGAAG | GTAACTGGCT | TCAGCAGAGC | GCAGATACCA | AATACTGTCC | 1380 |
| TTCTAGTGTA | GCCGTAGTTA | GGCCACCACT | TCAAGAACTC | TGTAGCACCG | CCTACATACC | 1440 |
| TCGCTCTGCT | AATCCTGTTA | CCAGTGGCTG | CTGCCAGTGG | CGATAAGTCG | TGTCTTACCG | 1500 |
| GGTTGGACTC | AAGACGATAG | TTACCGGATA | AGGCGCAGCG | GTCGGGCTGA | ACGGGGGGTT | 1560 |
| CGTGCACACA | GCCCAGCTTG | GAGCGAACGA | CCTACACCGA | ACTGAGATAC | CTACAGCGTG | 1620 |
| AGCATTGAGA | AAGCGCCACG | CTTCCCGAAG | GGAGAAAGGC | GGACAGGTAT | CCGGTAAGCG | 1680 |
| GCAGGGTCGG | AACAGGAGAG | CGCACGAGGG | AGCTTCCAGG | GGGAAACGCC | TGGTATCTTT | 1740 |
| ATAGTCCTGT | CGGGTTTCGC | CACCTCTGAC | TTGAGCGTCG | ATTTTTGTGA | TGCTCGTCAG | 1800 |
| GGGGGCGGAG | CCTATGGAAA | AACGCCAGCA | ACGCGGCCTT | TTTACGGTTC | CTGGCCTTTT | 1860 |
| GCTGGCCTTT | TGCTCACATG | TTCTTTCCTG | CGTTATCCCC | TGATTCTGTG | GATAACCGTA | 1920 |
| TTACCGCCTT | TGAGTGAGCT | GATACCGCTC | GCCGCAGCCG | AACGACCGAG | CGCAGCGAGT | 1980 |
| CAGTGAGCGA | GGAAGCGGAA | GAGCGCCCAA | TACGCAAACC | GCCTCTCCCC | GCGCGTTGGC | 2040 |

-continued

| | | | | | |
|---|---|---|---|---|---|
| CGATTCATTA | ATGCAGAATT | GATCTCTCAC | CTACCAAACA | ATGCCCCCCT | GCAAAAAATA | 2100 |
| AATTCATATA | AAAAACATAC | AGATAACCAT | CTGCGGTGAT | AAATTATCTC | TGGCGGTGTT | 2160 |
| GACATAAATA | CCACTGGCGG | TGATACTGAG | CACATCAGCA | GGACGCACTG | ACCACCATGA | 2220 |
| ATTCAAGAAG | GAGATATACA | T ATG AGC | GAT AAA ATT | ATT CAC CTG | ACT GAC | 2271 |

```
                              Met  Ser  Asp  Lys  Ile  Ile  His  Leu  Thr  Asp
                               1                  5                        10

GAC  AGT  TTT  GAC  ACG  GAT  GTA  CTC  AAA  GCG  GAC  GGG  GCG  ATC  CTC  GTC       2319
Asp  Ser  Phe  Asp  Thr  Asp  Val  Leu  Lys  Ala  Asp  Gly  Ala  Ile  Leu  Val
                    15                       20                       25

GAT  TTC  TGG  GCA  GAG  TGG  TGC  GGT  CCG  TGC  AAA  ATG  ATC  GCC  CCG  ATT       2367
Asp  Phe  Trp  Ala  Glu  Trp  Cys  Gly  Pro  Cys  Lys  Met  Ile  Ala  Pro  Ile
                    30                       35                       40

CTG  GAT  GAA  ATC  GCT  GAC  GAA  TAT  CAG  GGC  AAA  CTG  ACC  GTT  GCA  AAA       2415
Leu  Asp  Glu  Ile  Ala  Asp  Glu  Tyr  Gln  Gly  Lys  Leu  Thr  Val  Ala  Lys
               45                       50                       55

CTG  AAC  ATC  GAT  CAA  AAC  CCT  GGC  ACT  GCG  CCG  AAA  TAT  GGC  ATC  CGT       2463
Leu  Asn  Ile  Asp  Gln  Asn  Pro  Gly  Thr  Ala  Pro  Lys  Tyr  Gly  Ile  Arg
     60                       65                       70

GGT  ATC  CCG  ACT  CTG  CTG  CTG  TTC  AAA  AAC  GGT  GAA  GTG  GCG  GCA  ACC       2511
Gly  Ile  Pro  Thr  Leu  Leu  Leu  Phe  Lys  Asn  Gly  Glu  Val  Ala  Ala  Thr
75                       80                       85                       90

AAA  GTG  GGT  GCA  CTG  TCT  AAA  GGT  CAG  TTG  AAA  GAG  TTC  CTC  GAC  GCT       2559
Lys  Val  Gly  Ala  Leu  Ser  Lys  Gly  Gln  Leu  Lys  Glu  Phe  Leu  Asp  Ala
                         95                       100                      105

AAC  CTG  GCC  GGT  TCT  GGT  TCT  GGT  GAT  GAC  GAT  GAC  AAA  GGT  CCA  CCA       2607
Asn  Leu  Ala  Gly  Ser  Gly  Ser  Gly  Asp  Asp  Asp  Asp  Lys  Gly  Pro  Pro
                    110                      115                      120

CCA  GGT  CCA  CCT  CGA  GTT  TCC  CCA  GAC  CCT  CGG  GCC  GAG  CTG  GAC  AGC       2655
Pro  Gly  Pro  Pro  Arg  Val  Ser  Pro  Asp  Pro  Arg  Ala  Glu  Leu  Asp  Ser
          125                      130                      135

ACC  GTG  CTC  CTG  ACC  CGC  TCT  CTC  CTG  GCG  GAC  ACG  CGG  CAG  CTG  GCT       2703
Thr  Val  Leu  Leu  Thr  Arg  Ser  Leu  Leu  Ala  Asp  Thr  Arg  Gln  Leu  Ala
     140                      145                      150

GCA  CAG  CTG  AGG  GAC  AAA  TTC  CCA  GCT  GAC  GGG  GAC  CAC  AAC  CTG  GAT       2751
Ala  Gln  Leu  Arg  Asp  Lys  Phe  Pro  Ala  Asp  Gly  Asp  His  Asn  Leu  Asp
155                      160                      165                      170

TCC  CTG  CCC  ACC  CTG  GCC  ATG  AGT  GCG  GGG  GCA  CTG  GGA  GCT  CTA  CAG       2799
Ser  Leu  Pro  Thr  Leu  Ala  Met  Ser  Ala  Gly  Ala  Leu  Gly  Ala  Leu  Gln
               175                      180                      185

CTC  CCA  GGT  GTG  CTG  ACA  AGG  CTG  CGA  GCG  GAC  CTA  CTG  TCC  TAC  CTG       2847
Leu  Pro  Gly  Val  Leu  Thr  Arg  Leu  Arg  Ala  Asp  Leu  Leu  Ser  Tyr  Leu
                    190                      195                      200

CGG  CAC  GTG  CAG  TGG  CTG  CGC  CGG  GCA  GGT  GGC  TCT  TCC  CTG  AAG  ACC       2895
Arg  His  Val  Gln  Trp  Leu  Arg  Arg  Ala  Gly  Gly  Ser  Ser  Leu  Lys  Thr
          205                      210                      215

CTG  GAG  CCC  GAG  CTG  GGC  ACC  CTG  CAG  GCC  CGA  CTG  GAC  CGG  CTG  CTG       2943
Leu  Glu  Pro  Glu  Leu  Gly  Thr  Leu  Gln  Ala  Arg  Leu  Asp  Arg  Leu  Leu
     220                      225                      230

CGC  CGG  CTG  CAG  CTC  CTG  ATG  TCC  CGC  CTG  GCC  CTG  CCC  CAG  CCA  CCC       2991
Arg  Arg  Leu  Gln  Leu  Leu  Met  Ser  Arg  Leu  Ala  Leu  Pro  Gln  Pro  Pro
235                      240                      245                      250

CCG  GAC  CCG  CCG  GCG  CCC  CCG  CTG  GCG  CCC  CCC  TCC  TCA  GCC  TGG  GGG       3039
Pro  Asp  Pro  Pro  Ala  Pro  Pro  Leu  Ala  Pro  Pro  Ser  Ser  Ala  Trp  Gly
               255                      260                      265

GGC  ATC  AGG  GCC  GCC  CAC  GCC  ATC  CTG  GGG  GGG  CTG  CAC  CTG  ACA  CTT       3087
Gly  Ile  Arg  Ala  Ala  His  Ala  Ile  Leu  Gly  Gly  Leu  His  Leu  Thr  Leu
                    270                      275                      280

GAC  TGG  GCC  GTG  AGG  GGA  CTG  CTG  CTG  CTG  AAG  ACT  CGG  CTG  TGAAAGCTTA       3139
Asp  Trp  Ala  Val  Arg  Gly  Leu  Leu  Leu  Leu  Lys  Thr  Arg  Leu
          285                      290                      295
```

-continued

```
TCGATACCGT CGACCTGCAG TAATCGTACA GGGTAGTACA AATAAAAAAG GCACGTCAGA      3199
TGACGTGCCT TTTTTCTTGT GAGCAGTAAG CTTGGCACTG GCCGTCGTTT TACAACGTCG      3259
TGACTGGGAA AACCCTGGCG TTACCCAACT TAATCGCCTT GCAGCACATC CCCCTTTCGC      3319
CAGCTGGCGT AATAGCGAAG AGGCCCGCAC CGATCGCCCT TCCCAACAGT TGCGCAGCCT      3379
GAATGGCGAA TGGCGCCTGA TGCGGTATTT TCTCCTTACG CATCTGTGCG GTATTTCACA      3439
CCGCATATAT GGTGCACTCT CAGTACAATC TGCTCTGATG CCGCATAGTT AAGCCAGCCC      3499
CGACACCCGC CAACACCCGC TGACGCGCCC TGACGGGCTT GTCTGCTCCC GGCATCCGCT      3559
TACAGACAAG CTGTGACCGT CTCCGGGAGC TGCATGTGTC AGAGGTTTTC ACCGTCATCA      3619
CCGAAACGCG CGA                                                         3632
```

( 2 ) INFORMATION FOR SEQ ID NO:14:

( i ) SEQUENCE CHARACTERISTICS:
        ( A ) LENGTH: 296 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
               100                 105                 110

Ser Gly Asp Asp Asp Asp Lys Gly Pro Pro Gly Pro Pro Arg Val
           115                 120                 125

Ser Pro Asp Pro Arg Ala Glu Leu Asp Ser Thr Val Leu Leu Thr Arg
       130                 135                 140

Ser Leu Leu Ala Asp Thr Arg Gln Leu Ala Ala Gln Leu Arg Asp Lys
145                 150                 155                 160

Phe Pro Ala Asp Gly Asp His Asn Leu Asp Ser Leu Pro Thr Leu Ala
               165                 170                 175

Met Ser Ala Gly Ala Leu Gly Ala Leu Gln Leu Pro Gly Val Leu Thr
           180                 185                 190

Arg Leu Arg Ala Asp Leu Leu Ser Tyr Leu Arg His Val Gln Trp Leu
       195                 200                 205

Arg Arg Ala Gly Gly Ser Ser Leu Lys Thr Leu Glu Pro Glu Leu Gly
   210                 215                 220

Thr Leu Gln Ala Arg Leu Asp Arg Leu Leu Arg Arg Leu Gln Leu Leu
225                 230                 235                 240

Met Ser Arg Leu Ala Leu Pro Gln Pro Pro Asp Pro Pro Ala Pro
               245                 250                 255

Pro Leu Ala Pro Pro Ser Ser Ala Trp Gly Gly Ile Arg Ala Ala His
           260                 265                 270
```

| Ala | Ile | Leu | Gly | Gly | Leu | His | Leu | Thr | Leu | Asp | Trp | Ala | Val | Arg | Gly |
|---|---|---|---|---|---|---|---|---|---|---|---|---|---|---|---|
| | | 275 | | | | 280 | | | | | 285 | | | | |

| Leu | Leu | Leu | Leu | Lys | Thr | Arg | Leu |
|---|---|---|---|---|---|---|---|
| | 290 | | | | | 295 | |

( 2 ) INFORMATION FOR SEQ ID NO:15:

( i ) SEQUENCE CHARACTERISTICS:
        ( A ) LENGTH: 213 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..210

( x i ) SEQUENCE DESCRIPTION: SEQ ID NO:15:

| GCA | CCA | CTT | GCT | GCT | GAC | ACG | CCG | ACC | GCC | TGC | TGC | TTC | AGC | TAC | ACC | 48 |
|---|---|---|---|---|---|---|---|---|---|---|---|---|---|---|---|---|
| Ala | Pro | Leu | Ala | Ala | Asp | Thr | Pro | Thr | Ala | Cys | Cys | Phe | Ser | Tyr | Thr | |
| 1 | | | | 5 | | | | | 10 | | | | | 15 | | |

| TCC | CGA | CAG | ATT | CCA | CAG | AAT | TTC | ATA | GCT | GAC | TAC | TTT | GAG | ACG | AGC | 96 |
|---|---|---|---|---|---|---|---|---|---|---|---|---|---|---|---|---|
| Ser | Arg | Gln | Ile | Pro | Gln | Asn | Phe | Ile | Ala | Asp | Tyr | Phe | Glu | Thr | Ser | |
| | | | 20 | | | | | 25 | | | | | 30 | | | |

| AGC | CAG | TGC | TCC | AAG | CCC | AGT | GTC | ATC | TTC | CTA | ACC | AAG | AGA | GGC | CGG | 144 |
|---|---|---|---|---|---|---|---|---|---|---|---|---|---|---|---|---|
| Ser | Gln | Cys | Ser | Lys | Pro | Ser | Val | Ile | Phe | Leu | Thr | Lys | Arg | Gly | Arg | |
| | | 35 | | | | | 40 | | | | | 45 | | | | |

| CAG | GTC | TGT | GCT | GAC | CCC | AGT | GAG | GAG | TGG | GTC | CAG | AAA | TAC | GTC | AGT | 192 |
|---|---|---|---|---|---|---|---|---|---|---|---|---|---|---|---|---|
| Gln | Val | Cys | Ala | Asp | Pro | Ser | Glu | Glu | Trp | Val | Gln | Lys | Tyr | Val | Ser | |
| | 50 | | | | | 55 | | | | | 60 | | | | | |

| GAC | CTG | GAG | CTG | AGT | GCC | TAA | 213 |
|---|---|---|---|---|---|---|---|
| Asp | Leu | Glu | Leu | Ser | Ala | | |
| 65 | | | | 70 | | | |

( 2 ) INFORMATION FOR SEQ ID NO:16:

( i ) SEQUENCE CHARACTERISTICS:
        ( A ) LENGTH: 70 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| Ala | Pro | Leu | Ala | Ala | Asp | Thr | Pro | Thr | Ala | Cys | Cys | Phe | Ser | Tyr | Thr |
|---|---|---|---|---|---|---|---|---|---|---|---|---|---|---|---|
| 1 | | | | 5 | | | | | 10 | | | | | 15 | |

| Ser | Arg | Gln | Ile | Pro | Gln | Asn | Phe | Ile | Ala | Asp | Tyr | Phe | Glu | Thr | Ser |
|---|---|---|---|---|---|---|---|---|---|---|---|---|---|---|---|
| | | | 20 | | | | | 25 | | | | | 30 | | |

| Ser | Gln | Cys | Ser | Lys | Pro | Ser | Val | Ile | Phe | Leu | Thr | Lys | Arg | Gly | Arg |
|---|---|---|---|---|---|---|---|---|---|---|---|---|---|---|---|
| | | 35 | | | | | 40 | | | | | 45 | | | |

| Gln | Val | Cys | Ala | Asp | Pro | Ser | Glu | Glu | Trp | Val | Gln | Lys | Tyr | Val | Ser |
|---|---|---|---|---|---|---|---|---|---|---|---|---|---|---|---|
| | 50 | | | | | 55 | | | | | 60 | | | | |

| Asp | Leu | Glu | Leu | Ser | Ala |
|---|---|---|---|---|---|
| 65 | | | | 70 | |

( 2 ) INFORMATION FOR SEQ ID NO:17:

( i ) SEQUENCE CHARACTERISTICS:
        ( A ) LENGTH: 345 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:

(A) NAME/KEY: CDS
(B) LOCATION: 1..342

(xi) SEQUENCE DESCRIPTION: SEQ ID NO:17:

| | | | | | | | | | | | | | | | | |
|---|---|---|---|---|---|---|---|---|---|---|---|---|---|---|---|---|
| CAA | GCT | AAA | CAT | AAA | CAA | CGT | AAA | CGT | CTG | AAA | TCT | AGC | TGT | AAG | AGA | 48 |
| Gln | Ala | Lys | His | Lys | Gln | Arg | Lys | Arg | Leu | Lys | Ser | Ser | Cys | Lys | Arg | |
| 1 | | | | 5 | | | | | 10 | | | | | 15 | | |
| CAC | CCT | TTG | TAC | GTG | GAC | TTC | AGT | GAC | GTG | GGG | TGG | AAT | GAC | TGG | ATT | 96 |
| His | Pro | Leu | Tyr | Val | Asp | Phe | Ser | Asp | Val | Gly | Trp | Asn | Asp | Trp | Ile | |
| | | | 20 | | | | | 25 | | | | | 30 | | | |
| GTG | GCT | CCC | CCG | GGG | TAT | CAC | GCC | TTT | TAC | TGC | CAC | GGA | GAA | TGC | CCT | 144 |
| Val | Ala | Pro | Pro | Gly | Tyr | His | Ala | Phe | Tyr | Cys | His | Gly | Glu | Cys | Pro | |
| | | 35 | | | | | 40 | | | | | 45 | | | | |
| TTT | CCT | CTG | GCT | GAT | CAT | CTG | AAC | TCC | ACT | AAT | CAT | GCC | ATT | GTT | CAG | 192 |
| Phe | Pro | Leu | Ala | Asp | His | Leu | Asn | Ser | Thr | Asn | His | Ala | Ile | Val | Gln | |
| | 50 | | | | | 55 | | | | | 60 | | | | | |
| ACG | TTG | GTC | AAC | TCT | GTT | AAC | TCT | AAG | ATT | CCT | AAG | GCA | TGC | TGT | GTC | 240 |
| Thr | Leu | Val | Asn | Ser | Val | Asn | Ser | Lys | Ile | Pro | Lys | Ala | Cys | Cys | Val | |
| 65 | | | | | 70 | | | | | 75 | | | | | 80 | |
| CCG | ACA | GAA | CTC | AGT | GCT | ATC | TCG | ATG | CTG | TAC | CTT | GAC | GAG | AAT | GAA | 288 |
| Pro | Thr | Glu | Leu | Ser | Ala | Ile | Ser | Met | Leu | Tyr | Leu | Asp | Glu | Asn | Glu | |
| | | | | 85 | | | | | 90 | | | | | 95 | | |
| AAG | GTT | GTA | TTA | AAG | AAC | TAT | CAG | GAC | ATG | GTT | GTG | GAG | GGT | TGT | GGG | 336 |
| Lys | Val | Val | Leu | Lys | Asn | Tyr | Gln | Asp | Met | Val | Val | Glu | Gly | Cys | Gly | |
| | | | 100 | | | | | 105 | | | | | 110 | | | |
| TGT | CGC | TAG | | | | | | | | | | | | | | 345 |
| Cys | Arg | | | | | | | | | | | | | | | |

(2) INFORMATION FOR SEQ ID NO:18:

(i) SEQUENCE CHARACTERISTICS:
(A) LENGTH: 114 amino acids
(B) TYPE: amino acid
(D) TOPOLOGY: linear (ii) MOLECULE TYPE: protein (xi) SEQUENCE DESCRIPTION: SEQ ID NO:18:

| | | | | | | | | | | | | | | | |
|---|---|---|---|---|---|---|---|---|---|---|---|---|---|---|---|
| Gln | Ala | Lys | His | Lys | Gln | Arg | Lys | Arg | Leu | Lys | Ser | Ser | Cys | Lys | Arg |
| 1 | | | | 5 | | | | | 10 | | | | | 15 | |
| His | Pro | Leu | Tyr | Val | Asp | Phe | Ser | Asp | Val | Gly | Trp | Asn | Asp | Trp | Ile |
| | | | 20 | | | | | 25 | | | | | 30 | | |
| Val | Ala | Pro | Pro | Gly | Tyr | His | Ala | Phe | Tyr | Cys | His | Gly | Glu | Cys | Pro |
| | | 35 | | | | | 40 | | | | | 45 | | | |
| Phe | Pro | Leu | Ala | Asp | His | Leu | Asn | Ser | Thr | Asn | His | Ala | Ile | Val | Gln |
| | 50 | | | | | 55 | | | | | 60 | | | | |
| Thr | Leu | Val | Asn | Ser | Val | Asn | Ser | Lys | Ile | Pro | Lys | Ala | Cys | Cys | Val |
| 65 | | | | | 70 | | | | | 75 | | | | | 80 |
| Pro | Thr | Glu | Leu | Ser | Ala | Ile | Ser | Met | Leu | Tyr | Leu | Asp | Glu | Asn | Glu |
| | | | | 85 | | | | | 90 | | | | | 95 | |
| Lys | Val | Val | Leu | Lys | Asn | Tyr | Gln | Asp | Met | Val | Val | Glu | Gly | Cys | Gly |
| | | | 100 | | | | | 105 | | | | | 110 | | |
| Cys | Arg | | | | | | | | | | | | | | |

(2) INFORMATION FOR SEQ ID NO:19:

(i) SEQUENCE CHARACTERISTICS:
(A) LENGTH: 561 base pairs
(B) TYPE: nucleic acid
(C) STRANDEDNESS: double
(D) TOPOLOGY: unknown (ii) MOLECULE TYPE: DNA (genomic)

( i x ) FEATURE:
   ( A ) NAME/KEY: CDS
   ( B ) LOCATION: 1..558

( x i ) SEQUENCE DESCRIPTION: SEQ ID NO:19:

| | | | | | | | | | | | | | | | | |
|---|---|---|---|---|---|---|---|---|---|---|---|---|---|---|---|---|
| ATG | GCT | CCA | GTA | CCT | CCA | GGT | GAA | GAT | TCT | AAA | GAT | GTA | GCC | GCC | CCA | 48 |
| Met | Ala | Pro | Val | Pro | Pro | Gly | Glu | Asp | Ser | Lys | Asp | Val | Ala | Ala | Pro | |
| 1 | | | | 5 | | | | | 10 | | | | | 15 | | |
| CAC | AGA | CAG | CCA | CTC | ACC | TCT | TCA | GAA | CGA | ATT | GAC | AAA | CAA | ATT | CGG | 96 |
| His | Arg | Gln | Pro | Leu | Thr | Ser | Ser | Glu | Arg | Ile | Asp | Lys | Gln | Ile | Arg | |
| | | | 20 | | | | | 25 | | | | | 30 | | | |
| TAC | ATC | CTC | GAC | GGC | ATC | TCA | GCC | CTG | AGA | AAG | GAG | ACA | TGT | AAC | AAG | 144 |
| Tyr | Ile | Leu | Asp | Gly | Ile | Ser | Ala | Leu | Arg | Lys | Glu | Thr | Cys | Asn | Lys | |
| | | 35 | | | | | 40 | | | | | 45 | | | | |
| AGT | AAC | ATG | TGT | GAA | AGC | AGC | AAA | GAG | GCA | CTG | GCA | GAA | AAC | AAC | CTG | 192 |
| Ser | Asn | Met | Cys | Glu | Ser | Ser | Lys | Glu | Ala | Leu | Ala | Glu | Asn | Asn | Leu | |
| | 50 | | | | | 55 | | | | | 60 | | | | | |
| AAC | CTT | CCA | AAG | ATG | GCT | GAA | AAA | GAT | GGA | TGC | TTC | CAA | TCT | GGA | TTC | 240 |
| Asn | Leu | Pro | Lys | Met | Ala | Glu | Lys | Asp | Gly | Cys | Phe | Gln | Ser | Gly | Phe | |
| 65 | | | | | 70 | | | | | 75 | | | | | 80 | |
| AAT | GAG | GAG | ACT | TGC | CTG | GTG | AAA | ATC | ATC | ACT | GGT | CTT | TTG | GAG | TTT | 288 |
| Asn | Glu | Glu | Thr | Cys | Leu | Val | Lys | Ile | Ile | Thr | Gly | Leu | Leu | Glu | Phe | |
| | | | | 85 | | | | | 90 | | | | | 95 | | |
| GAG | GTA | TAC | CTA | GAG | TAC | CTC | CAG | AAC | AGA | TTT | GAG | AGT | AGT | GAG | GAA | 336 |
| Glu | Val | Tyr | Leu | Glu | Tyr | Leu | Gln | Asn | Arg | Phe | Glu | Ser | Ser | Glu | Glu | |
| | | | 100 | | | | | 105 | | | | | 110 | | | |
| CAA | GCC | AGA | GCT | GTG | CAG | ATG | AGT | ACA | AAA | GTC | CTG | ATC | CAG | TTC | CTG | 384 |
| Gln | Ala | Arg | Ala | Val | Gln | Met | Ser | Thr | Lys | Val | Leu | Ile | Gln | Phe | Leu | |
| | | 115 | | | | | 120 | | | | | 125 | | | | |
| CAG | AAA | AAG | GCA | AAG | AAT | CTA | GAT | GCA | ATA | ACC | ACC | CCT | GAC | CCA | ACC | 432 |
| Gln | Lys | Lys | Ala | Lys | Asn | Leu | Asp | Ala | Ile | Thr | Thr | Pro | Asp | Pro | Thr | |
| | 130 | | | | | 135 | | | | | 140 | | | | | |
| ACA | AAT | GCC | AGC | CTG | CTG | ACG | AAG | CTG | CAG | GCA | CAG | AAC | CAG | TGG | CTG | 480 |
| Thr | Asn | Ala | Ser | Leu | Leu | Thr | Lys | Leu | Gln | Ala | Gln | Asn | Gln | Trp | Leu | |
| 145 | | | | | 150 | | | | | 155 | | | | | 160 | |
| CAG | GAC | ATG | ACA | ACT | CAT | CTC | ATT | CTG | CGC | AGC | TTT | AAG | GAG | TTC | CTG | 528 |
| Gln | Asp | Met | Thr | Thr | His | Leu | Ile | Leu | Arg | Ser | Phe | Lys | Glu | Phe | Leu | |
| | | | | 165 | | | | | 170 | | | | | 175 | | |
| CAG | TCC | AGC | CTG | AGG | GCT | CTT | CGG | CAA | ATG | TAG | | | | | | 561 |
| Gln | Ser | Ser | Leu | Arg | Ala | Leu | Arg | Gln | Met | | | | | | | |
| | | | 180 | | | | | 185 | | | | | | | | |

( 2 ) INFORMATION FOR SEQ ID NO:20:

( i ) SEQUENCE CHARACTERISTICS:
      ( A ) LENGTH: 186 amino acids
      ( B ) TYPE: amino acid
      ( D ) TOPOLOGY: linear ( i i ) MOLECULE TYPE: protein ( x i ) SEQUENCE DESCRIPTION: SEQ ID NO:20:

| | | | | | | | | | | | | | | | |
|---|---|---|---|---|---|---|---|---|---|---|---|---|---|---|---|
| Met | Ala | Pro | Val | Pro | Pro | Gly | Glu | Asp | Ser | Lys | Asp | Val | Ala | Ala | Pro |
| 1 | | | | 5 | | | | | 10 | | | | | 15 | |
| His | Arg | Gln | Pro | Leu | Thr | Ser | Ser | Glu | Arg | Ile | Asp | Lys | Gln | Ile | Arg |
| | | | 20 | | | | | 25 | | | | | 30 | | |
| Tyr | Ile | Leu | Asp | Gly | Ile | Ser | Ala | Leu | Arg | Lys | Glu | Thr | Cys | Asn | Lys |
| | | 35 | | | | | 40 | | | | | 45 | | | |
| Ser | Asn | Met | Cys | Glu | Ser | Ser | Lys | Glu | Ala | Leu | Ala | Glu | Asn | Asn | Leu |
| | 50 | | | | | 55 | | | | | 60 | | | | |
| Asn | Leu | Pro | Lys | Met | Ala | Glu | Lys | Asp | Gly | Cys | Phe | Gln | Ser | Gly | Phe |
| 65 | | | | | 70 | | | | | 75 | | | | | 80 |
| Asn | Glu | Glu | Thr | Cys | Leu | Val | Lys | Ile | Ile | Thr | Gly | Leu | Leu | Glu | Phe |

|  |  |  |  |  | 85 |  |  |  |  | 90 |  |  |  |  | 95 |  |
|---|---|---|---|---|---|---|---|---|---|---|---|---|---|---|---|---|

Glu Val Tyr Leu Glu Tyr Leu Gln Asn Arg Phe Glu Ser Ser Glu Glu
     100     105    110

Gln Ala Arg Ala Val Gln Met Ser Thr Lys Val Leu Ile Gln Phe Leu
  115     120     125

Gln Lys Lys Ala Lys Asn Leu Asp Ala Ile Thr Thr Pro Asp Pro Thr
 130     135     140

Thr Asn Ala Ser Leu Leu Thr Lys Leu Gln Ala Gln Asn Gln Trp Leu
145     150     155    160

Gln Asp Met Thr Thr His Leu Ile Leu Arg Ser Phe Lys Glu Phe Leu
    165     170     175

Gln Ser Ser Leu Arg Ala Leu Arg Gln Met
   180     185

( 2 ) INFORMATION FOR SEQ ID NO:21:

( i ) SEQUENCE CHARACTERISTICS:
  ( A ) LENGTH: 327 base pairs
  ( B ) TYPE: nucleic acid
  ( C ) STRANDEDNESS: double
  ( D ) TOPOLOGY: unknown ( i i ) MOLECULE TYPE: DNA (genomic)

( i x ) FEATURE:
  ( A ) NAME/KEY: CDS
  ( B ) LOCATION: 1..327
  ( D ) OTHER INFORMATION: /citation=( ( x ) PUBLICATION INFORMATION:
  ( A ) AUTHORS: Lim,
  ( C ) JOURNAL: J. Bacteriol.
  ( D ) VOLUME: 163
  ( F ) PAGES: 311-316
  ( G ) DATE: 1985
  ( K ) RELEVANT RESIDUES IN SEQ ID NO:21: FROM 1 TO 327

( x i ) SEQUENCE DESCRIPTION: SEQ ID NO:21:

```
ATG AGC GAT AAA ATT ATT CAC CTG ACT GAC GAC AGT TTT GAC ACG GAT       48
Met Ser Asp Lys Ile Ile His Leu Thr Asp Asp Ser Phe Asp Thr Asp
 1               5                  10                  15

GTA CTC AAA GCG GAC GGG GCG ATC CTC GTC GAT TTC TGG GCA GAG TGG       96
Val Leu Lys Ala Asp Gly Ala Ile Leu Val Asp Phe Trp Ala Glu Trp
              20                  25                  30

TGC GGT CCG TGC AAA ATG ATC GCC CCG ATT CTG GAT GAA ATC GCT GAC      144
Cys Gly Pro Cys Lys Met Ile Ala Pro Ile Leu Asp Glu Ile Ala Asp
          35                  40                  45

GAA TAT CAG GGC AAA CTG ACC GTT GCA AAA CTG AAC ATC GAT CAA AAC      192
Glu Tyr Gln Gly Lys Leu Thr Val Ala Lys Leu Asn Ile Asp Gln Asn
      50                  55                  60

CCT GGC ACT GCG CCG AAA TAT GGC ATC CGT GGT ATC CCG ACT CTG CTG      240
Pro Gly Thr Ala Pro Lys Tyr Gly Ile Arg Gly Ile Pro Thr Leu Leu
 65                  70                  75                  80

CTG TTC AAA AAC GGT GAA GTG GCG GCA ACC AAA GTG GGT GCA CTG TCT      288
Leu Phe Lys Asn Gly Glu Val Ala Ala Thr Lys Val Gly Ala Leu Ser
              85                  90                  95

AAA GGT CAG TTG AAA GAG TTC CTC GAC GCT AAC CTG GCC                  327
Lys Gly Gln Leu Lys Glu Phe Leu Asp Ala Asn Leu Ala
         100                 105
```

( 2 ) INFORMATION FOR SEQ ID NO:22:

( i ) SEQUENCE CHARACTERISTICS:
  ( A ) LENGTH: 109 amino acids
  ( B ) TYPE: amino acid
  ( D ) TOPOLOGY: linear ( i i ) MOLECULE TYPE: protein ( x i ) SEQUENCE DESCRIPTION: SEQ ID NO:22:

| Met | Ser | Asp | Lys | Ile | Ile | His | Leu | Thr | Asp | Asp | Ser | Phe | Asp | Thr | Asp |
|---|---|---|---|---|---|---|---|---|---|---|---|---|---|---|---|
| 1 | | | | 5 | | | | | 10 | | | | | 15 | |

| Val | Leu | Lys | Ala | Asp | Gly | Ala | Ile | Leu | Val | Asp | Phe | Trp | Ala | Glu | Trp |
|---|---|---|---|---|---|---|---|---|---|---|---|---|---|---|---|
| | | | 20 | | | | | 25 | | | | | 30 | | |

| Cys | Gly | Pro | Cys | Lys | Met | Ile | Ala | Pro | Ile | Leu | Asp | Glu | Ile | Ala | Asp |
|---|---|---|---|---|---|---|---|---|---|---|---|---|---|---|---|
| | | 35 | | | | | 40 | | | | | 45 | | | |

| Glu | Tyr | Gln | Gly | Lys | Leu | Thr | Val | Ala | Lys | Leu | Asn | Ile | Asp | Gln | Asn |
|---|---|---|---|---|---|---|---|---|---|---|---|---|---|---|---|
| | 50 | | | | | 55 | | | | | 60 | | | | |

| Pro | Gly | Thr | Ala | Pro | Lys | Tyr | Gly | Ile | Arg | Gly | Ile | Pro | Thr | Leu | Leu |
|---|---|---|---|---|---|---|---|---|---|---|---|---|---|---|---|
| 65 | | | | | 70 | | | | | 75 | | | | | 80 |

| Leu | Phe | Lys | Asn | Gly | Glu | Val | Ala | Ala | Thr | Lys | Val | Gly | Ala | Leu | Ser |
|---|---|---|---|---|---|---|---|---|---|---|---|---|---|---|---|
| | | | | 85 | | | | | 90 | | | | | 95 | |

| Lys | Gly | Gln | Leu | Lys | Glu | Phe | Leu | Asp | Ala | Asn | Leu | Ala |
|---|---|---|---|---|---|---|---|---|---|---|---|---|
| | | | 100 | | | | | 105 | | | | |

( 2 ) INFORMATION FOR SEQ ID NO:23:

( i ) SEQUENCE CHARACTERISTICS:
        ( A ) LENGTH: 669 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..669

( x i ) SEQUENCE DESCRIPTION: SEQ ID NO:23:

| GAA | GAA | GTT | TCT | GAA | TAT | TGT | AGC | CAC | ATG | ATT | GGG | AGT | GGA | CAC | CTG | 48 |
|---|---|---|---|---|---|---|---|---|---|---|---|---|---|---|---|---|
| Glu | Glu | Val | Ser | Glu | Tyr | Cys | Ser | His | Met | Ile | Gly | Ser | Gly | His | Leu | |
| 1 | | | | 5 | | | | | 10 | | | | | 15 | | |

| CAG | TCT | CTG | CAG | CGG | CTG | ATT | GAC | AGT | CAG | ATG | GAG | ACC | TCG | TGC | CAA | 96 |
|---|---|---|---|---|---|---|---|---|---|---|---|---|---|---|---|---|
| Gln | Ser | Leu | Gln | Arg | Leu | Ile | Asp | Ser | Gln | Met | Glu | Thr | Ser | Cys | Gln | |
| | | | 20 | | | | | 25 | | | | | 30 | | | |

| ATT | ACA | TTT | GAG | TTT | GTA | GAC | CAG | GAA | CAG | TTG | AAA | GAT | CCA | GTG | TGC | 144 |
|---|---|---|---|---|---|---|---|---|---|---|---|---|---|---|---|---|
| Ile | Thr | Phe | Glu | Phe | Val | Asp | Gln | Glu | Gln | Leu | Lys | Asp | Pro | Val | Cys | |
| | | | 35 | | | | | 40 | | | | | 45 | | | |

| TAC | CTT | AAG | AAG | GCA | TTT | CTC | CTG | GTA | CAA | GAC | ATA | ATG | GAG | GAC | ACC | 192 |
|---|---|---|---|---|---|---|---|---|---|---|---|---|---|---|---|---|
| Tyr | Leu | Lys | Lys | Ala | Phe | Leu | Leu | Val | Gln | Asp | Ile | Met | Glu | Asp | Thr | |
| | 50 | | | | | 55 | | | | | 60 | | | | | |

| ATG | CGC | TTC | AGA | GAT | AAC | ACC | CCC | AAT | GCC | ATC | GCC | ATT | GTG | CAG | CTG | 240 |
|---|---|---|---|---|---|---|---|---|---|---|---|---|---|---|---|---|
| Met | Arg | Phe | Arg | Asp | Asn | Thr | Pro | Asn | Ala | Ile | Ala | Ile | Val | Gln | Leu | |
| 65 | | | | | 70 | | | | | 75 | | | | | 80 | |

| CAG | GAA | CTC | TCT | TTG | AGG | CTG | AAG | AGC | TGC | TTC | ACC | AAG | GAT | TAT | GAA | 288 |
|---|---|---|---|---|---|---|---|---|---|---|---|---|---|---|---|---|
| Gln | Glu | Leu | Ser | Leu | Arg | Leu | Lys | Ser | Cys | Phe | Thr | Lys | Asp | Tyr | Glu | |
| | | | | 85 | | | | | 90 | | | | | 95 | | |

| GAG | CAT | GAC | AAG | GCC | TGC | GTC | CGA | ACT | TTC | TAT | GAG | ACA | CCT | CTC | CAG | 336 |
|---|---|---|---|---|---|---|---|---|---|---|---|---|---|---|---|---|
| Glu | His | Asp | Lys | Ala | Cys | Val | Arg | Thr | Phe | Tyr | Glu | Thr | Pro | Leu | Gln | |
| | | | 100 | | | | | 105 | | | | | 110 | | | |

| TTG | CTG | GAG | AAG | GTC | AAG | AAT | GTC | TTT | AAT | GAA | ACA | AAG | AAT | CTC | CTT | 384 |
|---|---|---|---|---|---|---|---|---|---|---|---|---|---|---|---|---|
| Leu | Leu | Glu | Lys | Val | Lys | Asn | Val | Phe | Asn | Glu | Thr | Lys | Asn | Leu | Leu | |
| | | 115 | | | | | 120 | | | | | 125 | | | | |

| GAC | AAG | GAC | TGG | AAT | ATT | TTC | AGC | AAG | AAC | TGC | AAC | AAC | AGC | TTT | GCT | 432 |
|---|---|---|---|---|---|---|---|---|---|---|---|---|---|---|---|---|
| Asp | Lys | Asp | Trp | Asn | Ile | Phe | Ser | Lys | Asn | Cys | Asn | Asn | Ser | Phe | Ala | |
| | 130 | | | | | 135 | | | | | 140 | | | | | |

| GAA | TGC | TCC | AGC | CAA | GAT | GTG | GTG | ACC | AAG | CCT | GAT | TGC | AAC | TGC | CTG | 480 |
|---|---|---|---|---|---|---|---|---|---|---|---|---|---|---|---|---|
| Glu | Cys | Ser | Ser | Gln | Asp | Val | Val | Thr | Lys | Pro | Asp | Cys | Asn | Cys | Leu | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| TAC | CCC | AAA | GCC | ATC | CCT | AGC | AGT | GAC | CCG | GCC | TCT | GTC | TCC | CCT | CAT | 528 |
| Tyr | Pro | Lys | Ala | Ile 165 | Pro | Ser | Ser | Asp | Pro 170 | Ala | Ser | Val | Ser | Pro 175 | His | |
| CAG | CCC | CTC | GCC | CCC | TCC | ATG | GCC | CCT | GTG | GCT | GGC | TTG | ACC | TGG | GAG | 576 |
| Gln | Pro | Leu | Ala 180 | Pro | Ser | Met | Ala | Pro 185 | Val | Ala | Gly | Leu | Thr 190 | Trp | Glu | |
| GAC | TCT | GAG | GGA | ACT | GAG | GGC | AGC | TCC | CTC | TTG | CCT | GGT | GAG | CAG | CCC | 624 |
| Asp | Ser | Glu 195 | Gly | Thr | Glu | Gly | Ser 200 | Ser | Leu | Leu | Pro | Gly 205 | Glu | Gln | Pro | |
| CTG | CAC | ACA | GTG | GAT | CCA | GGC | AGT | GCC | AAG | CAG | CGG | CCA | CCC | AGG | | 669 |
| Leu | His 210 | Thr | Val | Asp | Pro | Gly 215 | Ser | Ala | Lys | Gln | Arg 220 | Pro | Pro | Arg | | |

( 2 ) INFORMATION FOR SEQ ID NO:24:

( i ) SEQUENCE CHARACTERISTICS:
        ( A ) LENGTH: 223 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

| | | | | | | | | | | | | | | |
|---|---|---|---|---|---|---|---|---|---|---|---|---|---|---|
| Glu 1 | Glu | Val | Ser | Glu 5 | Tyr | Cys | Ser | His | Met 10 | Ile | Gly | Ser | Gly | His 15 | Leu |
| Gln | Ser | Leu | Gln 20 | Arg | Leu | Ile | Asp | Ser 25 | Gln | Met | Glu | Thr | Ser 30 | Cys | Gln |
| Ile | Thr | Phe 35 | Glu | Phe | Val | Asp | Gln 40 | Glu | Gln | Leu | Lys | Asp 45 | Pro | Val | Cys |
| Tyr | Leu 50 | Lys | Lys | Ala | Phe | Leu 55 | Leu | Val | Gln | Asp | Ile 60 | Met | Glu | Asp | Thr |
| Met 65 | Arg | Phe | Arg | Asp | Asn 70 | Thr | Pro | Asn | Ala | Ile 75 | Ala | Ile | Val | Gln | Leu 80 |
| Gln | Glu | Leu | Ser | Leu 85 | Arg | Leu | Lys | Ser | Cys 90 | Phe | Thr | Lys | Asp | Tyr 95 | Glu |
| Glu | His | Asp | Lys 100 | Ala | Cys | Val | Arg | Thr 105 | Phe | Tyr | Glu | Thr | Pro 110 | Leu | Gln |
| Leu | Leu | Glu 115 | Lys | Val | Lys | Asn | Val 120 | Phe | Asn | Glu | Thr | Lys 125 | Asn | Leu | Leu |
| Asp | Lys 130 | Asp | Trp | Asn | Ile | Phe 135 | Ser | Lys | Asn | Cys | Asn 140 | Asn | Ser | Phe | Ala |
| Glu 145 | Cys | Ser | Ser | Gln | Asp 150 | Val | Val | Thr | Lys | Pro 155 | Asp | Cys | Asn | Cys | Leu 160 |
| Tyr | Pro | Lys | Ala | Ile 165 | Pro | Ser | Ser | Asp | Pro 170 | Ala | Ser | Val | Ser | Pro 175 | His |
| Gln | Pro | Leu | Ala 180 | Pro | Ser | Met | Ala | Pro 185 | Val | Ala | Gly | Leu | Thr 190 | Trp | Glu |
| Asp | Ser | Glu 195 | Gly | Thr | Glu | Gly | Ser 200 | Ser | Leu | Leu | Pro | Gly 205 | Glu | Gln | Pro |
| Leu | His 210 | Thr | Val | Asp | Pro | Gly 215 | Ser | Ala | Lys | Gln | Arg 220 | Pro | Pro | Arg | |

What is claimed is:

1. Fusion DNA having a formula selected from the group consisting of R1-R2, R2-R1, R1-L-R2 and R2-L-R1 wherein, R1 is thioredoxin-like DNA; R2 is eukaryotic DNA fused in frame and encoding a selected, desired protein; and L is linker DNA fused in frame and encoding a proteolytic cleavage site between the polypeptides encoded by R1 and R2 and preventing steric hindrance therebetween, said thioredoxin-like DNA being characterized by encoding a polypeptide that (1) has a three-dimensional structure substantially similar to that of *E. coli* thioredoxin and (2) contains an active site loop functionally and structurally equivalent to the double cysteine containing active site loop of *E. coli* thioredoxin.

2. Fusion DNA comprising (1) thioredoxin-like DNA, said thioredoxin-like DNA characterized by encoding a polypeptide that (a) has a three-dimensional structure substantially similar to that of *E. coli* thioredoxin and (b) contains an active site loop functionally and structurally equivalent to the double cysteine containing active site loop of *E. coli* thioredoxin; and (2) DNA encoding a selected, desired protein or peptide and fused in frame within said active site of said thioredoxin-like DNA.

3. The fusion DNA of claim 2 additionally comprising a linker DNA encoding a proteolytic cleavage site and fused in frame between said thioredoxin-like DNA and said selected, desired DNA.

4. The fusion DNA of claim 1 wherein R1 is selected from the group consisting of a DNA encoding thioredoxin, glutaredoxin, and the thioredoxin-like domains of protein disulfide isomerase, form-1 phosphoinositide-specific phospholipase C, and ERp72.

5. The fusion DNA of claim 3 wherein R1 is selected from the group consisting of a DNA encoding thioredoxin, glutaredoxin, and the thioredoxin-like domains of protein disulfide isomerase, form-1 phosphoinositide-specific phospholipase C, and ERp72.

6. The fusion DNA of claim 1 wherein R2 is selected from the group consisting of a DNA encoding IL-11, IL-6, M-CSF, MIP-1α and BMP-2.

7. Fusion DNA having a formula selected from the group consisting of R1-R2, R2-R1, R1-L-R2 and R2-L-R1 wherein, R1 is DNA encoding *E. coli* thioredoxin; R2 is eukaryotic DNA fused in frame and encoding a selected, desired protein; and L is linker DNA fused in frame and encoding a proteolytic cleavage site between the polypeptides encoded by R1 and R2 and preventing steric hindrance therebetween.

8. The fusion DNA of claim 7 wherein R2 is selected from the group consisting of a DNA encoding IL-11, IL-6, M-CSF, MIP-1α and BMP-2.

9. The fusion DNA of claim 7 wherein R2 is a DNA encoding IL-11.

10. Fusion DNA having a formula R1-L-R2, wherein R1 is DNA encoding *E. coli* thioredoxin; R2 is in frame DNA encoding IL-11 and L is in frame linker DNA encoding G-S-G-S-G-D-D-D-D-K (amino acids 110–119 of SEQ ID No. 14).

11. The fusion DNA of claim 10 wherein DNA encoding IL-11 comprises nucleotides 2599 through 3132 of FIG. 1.

12. An expression vector comprising a DNA of claim 1.

13. An expression vector comprising a DNA of claim 4.

14. An expression vector comprising a DNA of claim 5.

15. An expression vector comprising a DNA of claim 7.

16. An expression vector comprising a DNA of claim 8.

17. An expression vector comprising a DNA of claim 10.

18. A host cell containing an expression vector of claim 13.

19. A host cell containing an expression vector of claim 14.

20. A host cell containing an expression vector of claim 15.

21. A host cell containing an expression vector of claim 17.

22. The host cell of claims 18, 19, 20 or 21 wherein said host cell is a bacterial host cell.

23. The host cell of claim 22 wherein said bacterial host cell is an *E. coli* bacterial host cell.

24. The host cell of claims 18, 19, 20 or 21 wherein said host cell is a yeast host cell.

25. A method of producing a selected recombinant protein comprising culturing under suitable culture conditions promoting protein production a host cell containing a DNA of claims 4, 6, 7 or 10 and recovering said selected recombinant protein from the culture medium.

26. The method according to claim 25 wherein said recovering step comprises treating said host cells by osmotic shock to release said protein from the cell.

27. The method according to claim 25 wherein said recovering step comprises treating said host cells by freezing and thawing to release said protein from the cell.

28. The method of claim 25 wherein said DNA comprises the DNA of claim 8.

29. The method of claim 25 wherein said DNA comprises the DNA of claim 9.

30. The method of claim 25 wherein said DNA comprises the DNA of claim 11.

* * * * *